(12) United States Patent
Lightfoot et al.

(10) Patent No.: US 7,288,386 B2
(45) Date of Patent: Oct. 30, 2007

(54) METHOD OF DETERMINING SOYBEAN SUDDEN DEATH SYNDROME RESISTANCE IN A SOYBEAN PLANT

(75) Inventors: David A. Lightfoot, Carbondale, IL (US); Paul T. Gibson, Carbondale, IL (US); Khalid Meksem, Carbondale, IL (US)

(73) Assignee: Southern Illinois University, Carbondale, IL (US)

( * ) Notice: Subject to any disclaimer, the term of this patent is extended or adjusted under 35 U.S.C. 154(b) by 138 days.

(21) Appl. No.: 09/954,773

(22) Filed: Sep. 18, 2001

(65) Prior Publication Data

US 2002/0129402 A1 Sep. 12, 2002

Related U.S. Application Data

(63) Continuation of application No. 09/007,119, filed on Jan. 14, 1998, now Pat. No. 6,300,541.

(60) Provisional application No. 60/035,335, filed on Jan. 14, 1997.

(51) Int. Cl.
*C12Q 1/06* (2006.01)
(52) U.S. Cl. .................................................. 435/49
(58) Field of Classification Search ................ 435/29, 435/34, 39
See application file for complete search history.

(56) References Cited

U.S. PATENT DOCUMENTS

| | | |
|---|---|---|
| 5,385,835 A | 1/1995 | Helentjaris et al. |
| 5,476,524 A | 12/1995 | Leon et al. |
| 5,491,081 A | 2/1996 | Webb |
| 5,492,547 A | 2/1996 | Johnson |
| 5,536,901 A | 7/1996 | Greaves et al. |
| 5,574,210 A | 11/1996 | Saghai-Maroof et al. |
| 5,606,823 A | 3/1997 | Souza et al. |
| 5,612,191 A | 3/1997 | Briggs et al. |

OTHER PUBLICATIONS

Njiti et al 2001, Crop Science 41:1726:1731.*
Stephens et al 1993, Crop Science 33:63-66.*
Holliday, "A Dictionary of Plant Pathology," Cambridge University Press (Cambridge), p. 141, (1989).
Lewin, "When Does Homology Mean Something Else?," Science, p. 1570, (1987).
Njiti et al., "Soybean Response to Sudden Death Syndrome: Inheritance Influenced by Cyst Nematode Resistance in pyramid X Douglas Progenies," Crop Science, vol. 36 (No. 5), p. 1165-1170, (1996).

* cited by examiner

*Primary Examiner*—David H Kruse
(74) *Attorney, Agent, or Firm*—Jenkins, Wilson, Taylor & Hunt, P.A.

(57) ABSTRACT

A method of determining the presence of soybean sudden death syndrome resistance in the soybean plant in a greenhouse setting, the method comprising the steps of: (a) inoculating soil with a low density inoculum of *Fusarium solani*; (b) planting a soybean plant in said inoculated soil; (c) growing said plant in said soil in a greenhouse; (d) isolating *Fusarium solani*-infected tissue from said plant; (e) culturing said infected tissue for a period of time sufficient to allow for fungal colony forming unit growth; (f) scoring at least one of disease severity and infection severity in said plant using the number of said fungal colony forming units; and (g) correlating at least one of said disease severity and said infection severity to at least one of disease severity and infection severity data from genetic markers associated with soybean sudden death syndrome resistance to identify a correlation, wherein a statistically significant correlation indicates presence of soybean sudden death syndrome resistance in said soybean plant. Also provided is a method of characterizing resistance to soybean sudden death syndrome in a soybean plant, the method comprising the steps of: (a) isolating roots from a soybean plant infected by *Fusarium solani*; (b) culturing the root on a culture plate including a restrictive growth medium that provides for slow fungal growth and restricted bacterial growth; (c) determining root infection severity by statistically evaluating the number of *Fusarium solani* colony forming units on said culture plate; and (d) characterizing resistance to soybean sudden death syndrome in said soybean plant based on said determined root infection severity.

5 Claims, 23 Drawing Sheets

Figure 1A:
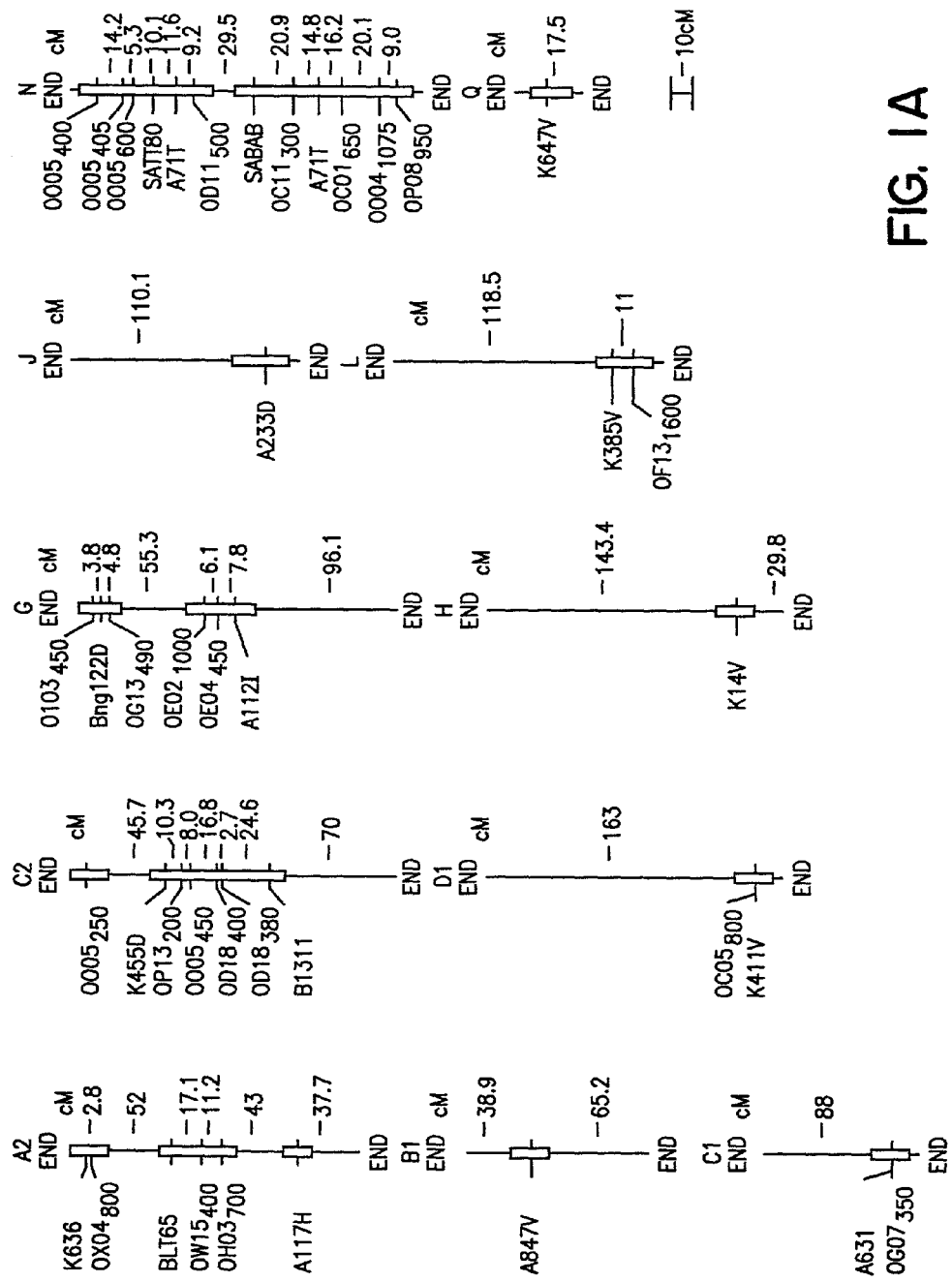

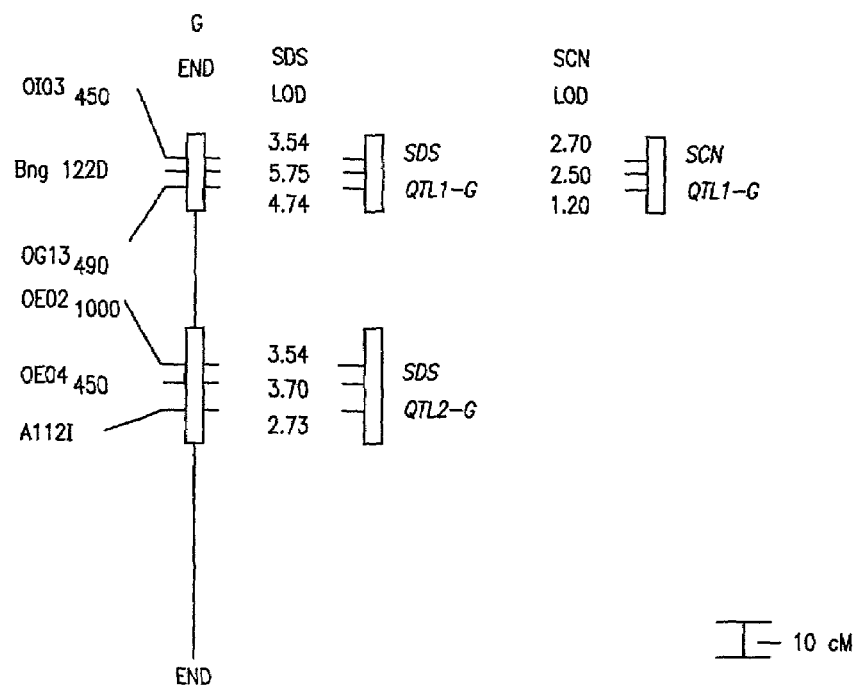
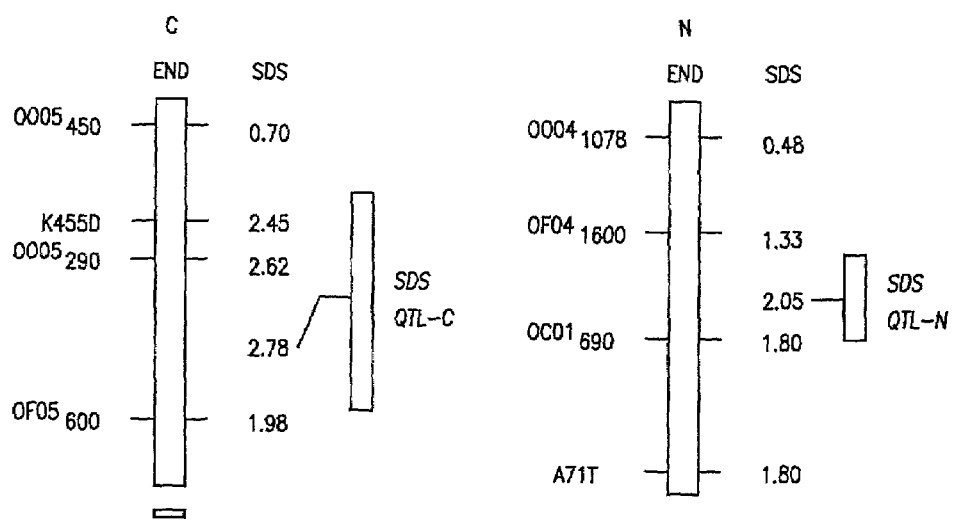
FIG. 1B

List Map of linkage group A:

|   |          |   |         |
|---|----------|---|---------|
|   | A117H    | - | 5 cM    |
|   | rfs2     | - | 38 cM   |
|   | OH03$_{700}$ | - | 11.2 cM |
| 5 | OW15$_{500}$ | - | 14 cM   |
|   | Blt65    | - | 1 cM    |
|   | CCAAGC309 | - | 0.5 cM |
|   | CCC/ATG349 | - | 0.1 cM |
|   | CCG/AAC400 | - | 0.4 cM |
| 10 | Rhg4    | - | 0.4 cM  |
|   | CCG/AAC401 | - | 0.1 cM |
|   | CAT/ATT250 | - | 0.5 cM |
|   | CCC/ATG350 | - | 0.5 cM |
|   | CCA/AGC310 | - | 2.8 cM |
| 15 | OX04800 | - | 50 cM   |
|   | K636     |   |         |

FIG. 1D

Sequence of OI03$_{450}$ Essex DNA, 527 bp (SEQ ID NO:1)

TGTTCTAGATAGTTCGCAATTCAATCAAATTTCCCAATTATAATTG

AATAAAAGATTCATGAAATCAGGTGATCAAGCGAAAAATAAGCAT

5 TAAGCGTAGAAGAGAAGCAATAACATTTTTTTATTAAATAATAAAA

GAGTAATTACATAAAATATGTTCGATTACATTAAACCCCAACAAA

GGATGAATTTAGCTTCTCATGACCATGGGGAAAATCAAACTTGATG

AACAAGAAGATGAAGAAGAATCCTTAAGGATAAACACTGCCTAGCT

CCAATGTGCTCTCTAGTATTTTATCTTTCAAAAATCCCCAAGAACC

10 CCTAATTTTCAGTAAGAAGCCCATTTTCAATCAGAAGCCCATTTTC

AATCAAGAAGCCCATTTTCAATCAGAAGCCCATTTTCAATCAGAAG

CCCATTTTCAATCAGAAGCCCATTTTCAATCAGAAGCCCATTTTAT

AATTGTATTCCCAAAACTTGAGATTCTTGAACGTAAATTATTAGTA

AATTGTAATCACCTCTGTAAA

FIG. 3A

Sequence of OI03$_{450}$ Forrest DNA, 814 bp (SEQ ID NO:2)

ATGATTACGCCAAGCTATTTAGGTGACACTACTAGAATACTCAAGCTATGCATCCAACG

CGTTGGGAGCTCTCCCATATGGTCGACCTGCAGGCGGCCGCACTAGTGATTCAGAAGCC

CAAAGGTAACAGCAATAAGTAATCCCTTGTTTATAAGATCCCAGAACTTCCAGTTTATT

TAATGAAAATGCAATAACATCGGCTAGTTTCACAAGTAATATACAAATCGGAACATCAC

ATTGACTACAATATATAGTACATAAATTAACACTAAGAAACCTCCTTGATTTGATATTA

TGCATTTACCTATGTTGTTCCACAAGAATATACTCAAATGACTTTGCCTTGATTTAAAT

TATCACGATGTAACACAAACAAAGATGATANTTTGTCGATCAACTGTTCAGCACCAAGA

GAGCCCTCCCCACAATCAACTCAGGTTTTCACTTTTGGTGCTTGAAAATGAGTGGCACA

TGNAAAAGCAAGAGTCNTCTTTGACAAATGTGCCTGCCGANAGTTATCANTACTTACTA

ACAAGATAATGAGCCAAAACATCATCTGGGNCATCAACCTTCATGNCTTTNTCAAGTTT

ATACCTATNANTNACTANGTCTTATATTTNCANNTGGTGATTACANTTACNANTAAGTT

TAGCTTNAAGAAATNCAAGTTTTNGGGACTCCATGCCTNGNCGGNTTTCNNATCCGTC

GGCCAGGGCGGNCGGNNCACTGNTNGGNAGNCCCANTTNCNCAGANCACNGNCCCNTT

TCCATTCCNGGNCCNTCNNCTTCAANGACNGCCGGNGAAANCNNGGGT

FIG. 3B

K455-T3      (SEQ. ID NO: 3)

GCAGATGTAACTGTTCCCACAATATCTAATATTCTAGTTCTAGATGAAAATATTTTTT
TCCCATAGCAAGCAAAGTATGGATTTGTCATTTTTCAGAGACGAAGAACTCTCAACA
AACATGTTTATAGTAACTTCATTGCAAAACTCAACAAATAGATTTTTGGAACCTTAAT
ATAATAAAATTCAACAGTCTTCTTTAATTTTATTCTGCTCTTACCTTCTCATAGGATCA
TATAGAATTTAACCCTACAAGCTCTCAAAAAACAATCCATTATTATGCTCCTTATCCA
ATAAAACAAAACCATAGAGTGATTCTCAAAATGAAGATTGACAAAGGCAAAAAGTTA
CAATCAATAATCTTAAATTGTGTACTTACTTATTCCTCGGGGNGCANATNCTTTGGAA
TGCTGGNTCAATAGCTTCTTTATAATTNTCTTCATCTTGCACCNTCCCNGCCTTAGGN
GGTCTCCATTGTCAATCCAAAGGTNNTCGN

FIG. 4

K4SS-T7      (SEQ. ID NO: 4)

GGTACCCGGGGATCCTCTAGAGTCGACCTGCAGGGAGGCGAATGTNATGTTGANCTT
TGCTCGCTCATATGGCCTTACAGGGTTTGCCGAATTAGTGTGAAGGTAATTCGGTAA
ATGGATAATATTGTATTCATTTNATATTTNATGATGTTACAAGTNCAAGGNATAANCT
GATGCCTGAGT

FIG. 5

A117-T3      (SEQ. ID NO: 5)

CAGGTAGACAAATCTGATGGTACTGAAGTTGGTCATACAATTAAAAAGTTCCCTCTTT
TAAAGCCCAGAGAATATGTGCTAGCTTGGAAGTNGTGGGAGGGGAGTGATGAAACA
TTTTACTGTTTTATGAAGGTAATACACCAATTATTATGGTTTTTTGTTTAATAAAATGT
GAATAATTGTCAATCGTGATTGCATTATCTCTCCTTTACTCTGTCTCTTCACCTTTTTT
ACCCTTTTATTTGAGAGGAAGAATCCATGTAGTAAAAAATGATGATAAAATTGTTAG
AAAATATAGTGTCATGTAATTAGAGATTCAGATTATAACTTAGAAGACACTATTATTT
TCATGTAATACTATCCACGGGTAATTAATCAATACTGACATATTTTCACTCAAAATATT
CTGGTTTTCTCATTATATACATTTAAATAGGAGCTATTANCCATTGCAAGCTTGGGTT
TGGAGGCCTTCCGATGCCTTGTTGGGATTGNGACCA

FIG. 6

A847-T3      (SEQ. ID NO: 6)

NAGNCAGGGAACCCACACATACAGACAATTAAAACCGTTGGATGAAAATCATACTAC
TCATAAATTGAAAATATATACGTAAGANCTTCATCTAACAGTGCTAGTCGAAGAATG
CGTAAATGCAGGNNATCCATTTCCATACTAAAATGGACAAAACTTATATTTTTTTTTT
AGCGGCAAACGTTAATTATTAATTTTTTTAGTACAAGGGATCAAACCANGACCTTTC
CCTTCTTTCCATCTTTCTTGACCACCCAACCAACCTTATATCTCCACAAAACTTATTAT
ATGTTGTTCTTCGGGGACTATCAGAATTGGAGTTTAACCTCGGGCANTCAATCTACAT
AATCCTTGATTTNATTTNGTGAAGTTCTAAAGCCACAGGCATTATTTATNTTATTNTT
TCTGNAGTAACCCNCCATATGTTGGTNNATAAGGGTANGNATNAAAATNCNTTGGNT
GGTNNCNATTTGCNCTTNCNAGGCCGGGGATGGNTTTT

FIG. 7

A847-T7      (SEQ. ID NO: 7)

NNACAANANANCAGGGGATCCTCTAGAGTCGACCTGCAGTGATACTAGAACTNAAT
GAACAGGGAGAGAGAGAGAGAGAGAGANANTNAANATAACGATGAAGCTCTCCCTATT
GACGGTGTTCATTGTAGCAATAGCATCGTTATCTCTTATTATTGCTGGTTCATCATNA
TCTCAATTCCAGTGGCA

FIG. 8

(SEQ ID NO:8)

AATTTTTTATATAAGTTGCAAAATTTAGGGACTTATTTATTATTAAATTATTTGTAGGG

ACTAATTTATCATATTTTTTGTATATTCAGGAATTAAATTTAATTTTTCATCCTTCAAT

ACTAACTTATTAACGTTTCACATTTTCAAAGACGAGTCTAGCTATTTATAATTTTTTTT

5    CCTAAAATATATTTTTTGTCCTCATAAATATGAAAATATTTAAAATTCGTTCCTAATTT

TTTTTTCAAAGCATCTTTCCTT<u>CTCACAAAATTGAAATGTATCA</u>TTTTTTTTTGTTCAA

AAGTTTAAATAAATTTGAACCTAATATGACATTTTATATCGGTTATACATATAACTGAT

ATAAACATCAAGTTTTTTATATCAATGATACCTATAACTGATATCAAATGTGACAATTA

TATATATAATTAATGTAAAAAGTCATAAATATAATTTATTTTGAGTCAAAAAATAATA

10   TATTTTAAT<u>TATTTTGAAGATGAAAAAGG</u>ATAAATTTAAAACATTTGTGTGANGATGAA

AAACTAGATGTTTTTTTTCCTGGTTTAAATGCAAAACCAATGCTATTTTATTTAAATTT

TACCTTTTTTTTATAATTACNCCACCAAAAAACCGTTTGGTGTTACAAATTTGANTTAA

ATTCTNTTGTTTATTAAAAGANANATTAATTNGGAANGGTCTTTTTNAAAACNCTNCN

GTCNANTAACNAATCT

FIG. 9

(SEQ ID NO:9)

ACGCCAGTGANTGTAATACGACTCCTATAGGGCGAATTGGCCAAGTCGGCCGAGCTCGA

ATTCGTCGACCTCGAGGGATCACGCTAATGATATATTATTAATCAACTGCTTCAATAGA

GTGCACACACCCTATCTTTCATAAAATTACTACACTTTTTAATTTTTGTAATAAAAAAC

CTAGAAAAACTCATTATGAAACAGATGATGTACTTTTAACACTCTGTCGGCCTCTCTCT

CTCTATTATATATTGATTTAAATTTATTGAGAATTATATTTTTGTTGGGTCTCATTTAT

TATATTTATTAATTGGATCCGGGCCCTCTAGATGCGGCCGCATGCATAAGCTTGAGTA

TTCTATAGTGTCACCTAAATAGCTTGGCGTAATCATGGTCATAGCTGTTTCCTGTGTGA

AATTGTTATCCGCTCACAATTCCACACAACATACGAGCCGGAAGCATAAAGTGTNAAGC

CTGGGGTNCCTAATGAGTGAGCTAACTCACATTAATTGCCTTGCGCTCACTGCCCGCTT

TCCAGTCNGGAAACCTGTCCTGCCAGCTGCATTAATGAATCNGCCAACCCNCGGGGANA

AGCNGTTTGCNTATGGGCGCTCTTNCCGCTTCCTCGCTCANTGACTCGCTGCGCTCNGT

CNTTCNGNTGCCGCGAACGGTATCANCNCACTCNAANGNNGTAAATACGGTTATCCACC

NAACCNNGGGGANAACCCNGGAAAAAACATGTNANCCAAAAGGCCNCCAAAAGGCCANG

AAACNTTNAAAAGGCCCNNTTGCTTGNCTTTNTN

FIG. 10

(SEQ ID NO:10)

NNNNNNNTTGTAAACGACGCAGTGAATGTATACGACCACTATAGGGCAATGGCCAAGTCG

GCCGAGCTCGAATTCGTCGACCTCGAGGGATCTTTTTATGTTGGTAGCTACTGTAATAT

CATCTTGTACTTTTAACTTTTAAGTCATACTCCCTTTGGACTCATATATAAGCAAAAGA

GTGGTCTTGTATGTCGGACTTAAATATAAGCAAATCTAACTAATTTTGTCCTATTTAAT

ACTTTCATTCCTAAAACACCCTTCATTTAATTCTAATTCTATTTCCAATAACTCTTTTT

TATTCATGATAACAAGTTCCAATGAAGGACATTTTAGAAATAACCTTATTTTTATTTG

AGATTAGTAAAATTAAATGATGTGAACTAACTTTCTTAATTAATGTGAAATTAGTTATT

TTTTCTTATATACGAGTCCAAAGGGAGTACCAAATTTCACAAATGTACTAAAATGTATT

ATATGCTTCTTTTTAATTCATCTTTGCTGCATANCTACTTAGCTACTGTGCTCTGATCC

GGGCCCTCTAGATGCGGCCGCATGCATAAGCTTGAGTATCTATAGTGTCCCTAAATAGC

TTGGCGTATCATGGTCATAGCTGTTTCCNGTGTGAAATTGTTATCCGCTCACAATTCCA

CACAACATACGANCCGGAAGCATAAAAGTGTTAAGCCNGGGGTGCCTAATGAGTGAGCT

AACTCACATTAATTGCGTTGCGCTCACTGCCCGCTTCCNATTCGGGAAACTGTCCTGNC

ANCTGCATTAATGAATCNGGCCAACCCNCNGGGAAAAGGCGG

FIG. 11

(SEQ ID NO:11)

ACNGCCAGTGAATTGTAATACGACTCCTATAGGGCGAATTGGCCAAGTCGGCCGAGCTC

GAATTCGTCGACCTCGAGGGATCTATAATATTTCTGACAGCTACCTTTTTATTTAGCTT

GCAGAGGGGCTGATTTTGGAGAAAACATCATCCATGGTATAAAGTCCGTTTAGATTCCA

5    GCTATTGTTCACATTCATCCCTTACATATGAGAATATCCCTATAAGCTGAAACTAACTT

TTACAAACAAACATGCACCGAACCATTAAAGTTTGACTTAATATCCGGGGTATAATGAC

CTTAATTCAGAAATTCACATAAATAACTAAAAGTAAGTTGTATTTTATTTATGTCTGGA

TTTACTGCACAAACTAAACAAAAGTTTGTGGATTTAGACATAAAAAATACCAATGCTGT

GTGAAAATAAGAAATGGTGGTCATATAGACAAGTTTCTTTTCTGTTTTCTTTAAATTGC

10   AGTCNAAGCCATCANGAGGTTCATGTAATTAACCAAACTAGACGTTGACTTTTGGTTTT

ATCCTTTTGTAGAATAGCAAGCAAGTCATTATAAATCTGGCCATTGGGACAGCTTAGTT

TAACTCCCGCCGCAAATTTGTTAAAATATTNAATAATAATATCACCTAAAATCATATTT

GTCANTTCATTTTGTTTTANGTTATATCAATTATTATTTTTACCTTACNTCCTTTATA

ATNTCAATGATGGGACCCAAAAAATTATCAAATACNTTNAAGCNTTATTTATTATTAAT

15   TAANCCTTTAATTATAATTAAAAATTCNATTTAATTTTTTAAN

FIG. 12

(SEQ ID NO:12)

ANANGATTCGNCAGCTATTTAGGTGACATATAGAAATACTCAAGCTTATGCATGCGGCC

GCATCTAGAGGGCCCGGATCTTTCGGTTGAAGCAAAATTGAAGTCTTTTGCTCATTTTT

ATCAAATTCTTTAATGAAAAGTTAATTACATAAAATATTTTAGTAGAAGCAATTTTACA

CAGTTATTATTTAAAAAAATTACACAGTTATTCAATAACAAATTACAATATATTATAAG

GTTATAATAAATATTTTAAAATTCATATAAAAGATGACTTATTAATAAGTTGATAATGT

AAATTTTTTACACTATTAAACTCATTTTACGTAATCTTAGCGACAACATACTATTTTTT

TCATGAAATTTACAAAAGCTTTCAAAAATAAAATTATTAGTTGTACCCCCAAAATATA

AAATTATTAGCTATGTTAAAAATTTGTGAATTTCATAAAAGAAAAAAATATTACAGTAT

TATATATTAAAATTAAATCTCACAATAAAAACACGTAAAGTTATCGTTTTGAATTATTA

GTTAAAGTCCTTCGTCTCGTATTTTTCTCAACTCTACCGACAGCATAAACAGGTTGTCT

CCTTCNTAATAACAATCGTGGCTGGGAACAAAAATCGTTTTTTTAGAAGAATCNGAAAT

CGTATTGACGGTGCGTTTTAAAAAGACTATCCAATAATCTTCTTTTAATAACNCTGAAT

TTCNCCAATTCTTNCNCAACGGTTTTTTGGTGCGTTNTTTTAAAAAAAGTTNAATTTAA

TTAAAATNCN

FIG. 13

(SEQ ID NO:13)

ATNCCCNAGCTATTAGGTGACACTATAGAATACTCAAGCTTATGCATGCGGCCGCATCT
AGAGGGCCCGGATCCAATTAATAAAATATAATAAATGAGACCAACNAAAATATATTCTC
NATAAATTTNAATCCATATTTTANTAAAAAAAAAAAGGCCNACAAATTNTTAAAATTCC
TNCNNCNNTTTCATANTNATTTTTCCTAGGTTTTTTATTNCAAAANTTAAAAATTNTAT
TANTTTTATNAAAAATAGGGTNTNTGCACNCTATTGAACCANTNNATTAATAATATATC
TTTANCNTNATCCCTCAAGGTCAACAAANTTCANANCNCGGCCNACTTGGCCAATTCNC
CCTATAGTGANTCNTNTTACAACTCACTGGCCGTCGTTTTACAACCTCGTGACTGGGAA
ANCCCTGGCGTTCCCCAANTTAATCNCCTTGCAACATNTCCCCTTTCGCCNGCTGGTGT
TNATACCNAAAAGGCCCGCNCCGATCGCCCTTCCCNACTTTTGCGCCCCCTNAATGGCN
AATGGACGCCCCTGTTNCGNGCNCATTANNCGCGGCGGGTGTGGTGGTTACCCCCACNT
GACCCTACACTTGCCAGCCCCCTAACCCCNCCCCTTTCGCTTTCTCCCCTCCTTTTCTC
GCCNCTTCGCCGGNTTCCCNTCAAGCNCTAAATCGGGGCTCCCTTTAGGGTTCCNAATT
AATTGCTTTACGGCCCTCCACCCCAAAAACTTGATAAGGGTGATGGTCNCNTTCTGGGG
CNNCCCCN

FIG. 14

(SEQ ID NO:14)

ACNTGATTCACCAAGCTATNTAGGTGACTATAGAATACTCAAGCTTATGCATGCGGCCG

CATCTAGAGGGCCCGGATCAGAGCACAGTAGCTAAGTAGCTATGCAGCAAAGATGAATT

AAAAAGAAGCATATAATACATTTTAGTACATTTGTGAAATTTGGTACTCCCTTTGGACT

CGTATATAAGAAAAAATAACTAATTTCACATTAATTAAGAAAGTTAGTTCACATCATTT

AATTTTACTAATCTCAAATAAAAAATAAGGTTATTTCTAAAATGTCCTTCATTGGAACT

TGTTATCATGAATAAAAAAGAGTTATTGGAAATAGAATTAGAATTAAATGAAGGGTGTT

TTAGGAATGAAAGTATTAAATAGGACAAAATTAGTTAGATTTGCTTATATTTAAGTCCG

ACATACAAGACCACTCTTTTGCTTATATATGAGTCCAAAGGGAGTATGACTTAAAAGTT

NAAAGTNCAAGATGATATTACAGTAGCTACCAACATAAAAAGATCCCTCGAGGTCGACG

AATTCGAGCTCGGCCGACTTGGCCAATTCCCCTATAGTGAGTCGTATTACAATTCACTG

GCCGTCGTTTTACAACGTCNTGACTGGGAAAACCTGGCGTTCCCCACTTATCGCCTTGC

AGCACATCCCCTTTCGCCNGCTGGCGTNNTACCAAAAAGGCCGCACCGATCGCCCTTCC

CNACAGTTGCCCCANCCTGAATGGCGAATGGACCCCCCTGTTACCGGCCCATTTAAAC

CCCGNNGGGTGTTGTGGTTNCCCCNCCCN

FIG. 15

(SEQ ID NO:15)

ATTACGCCAAGCTATTAGGTGACACTATAGAAATACTCAAGCTTATGCATGCGGCCGCA

TCTAGAGGGCCCGGATCTTTTATTAAAAATTTAATTGAGTCTCTTAATTATTGAAAAGT

TTAATTAAATCATCAATTATTAAAAAAAATCAACCATATCCTTTATTGTTTAAAACATT

ATAATTATGCTCTTTCAACCAACTCTGTTAGTTTAATTGATAGAAGTTTTGTAAATAGA

TATTTTTACATAATATAAATAATCTTTTTACATATATTGCAGCCAATGTAAAATATTAT

CTTTTTACATTCATTGCTTTTGATGTAAAAAATTATTGTTTTACATATGTTGTATTGAC

AATAAATATAAAAATATTTATTTTTGTCAATTAGATTAATGAACTGATGATGAAAAAGA

TATAATTATAATATTTTAATAATTAGAGAATTTGATTGAACTTTTTAATAATTAAAAA

ATTAAATGAATTTTTAATTATAATTAAAGGGATTAATTATATATATAAGCTTTAATGTA

TTTATAATTTTTGGTGTCCNCATTAATATTATAAAAGGATGTAAGTAAAAAATAATAAT

TAATATTACATAAACAAAATAAAATGACAATATTATTAGGTGATATTATTATTAATATT

TTAAACAAATTNCNGCGGAGTTAACTAAAGCTGTCCAATGGNCAGATTATAATGACTGC

CTGCNATTCTNCAAAAGGATAAAACAAAAGTCCACGTCTAGTTTGGGTAAATACATGAA

CCTCCNGAATGGCTT

FIG. 16

(SEQ ID NO:16)

ACATGATTACACAAGCTATTTAGGTGACATATAGAATACTCAAGCTTATGCATGCGGCC

GCATCTAGAGGGCCCGGATCGCCCTTCCCAACAGTTGCGCAGCCTGAATGGCGAATGGA

CGCGCCCTGTAGCGGCGCATTAAGCGCGGCGGGTGTGGTGGTTACGCGCAGCGTGACCG

CTACACTTGCCAGCGCCCTAGCGCCCGCTCCTTTCGCTTTCTTCCCTTCCTTTCTCGCC

ACGTTCGCCGGCTTTCCCCGTCAAGCTCTAAATCGGGGGCTCCCTTTAGGGTTCCGATT

TAGTGCTTTACGGCACCTCGACCCCAAAAAACTTGATTAGGGTGATGGTTCACGTANTG

GGCCATCGCCCTGATAGACNGTTTTTCGCCCTTTGACNTTGGAGTCCACGTTCTTTAAT

AGTGGACTCTTGTTCCAAACTGGAACAACACTCAACCCTATCTCGGTCTATTCTTTTGA

TTTATAAGGGATTTTGCCGATTTCGGCCTATTGGTTAAAAAATGAGCTGATTTAACAAA

AATTTNACGCGAATTTTAACAAAAATATTAACGCTTACNATTTCCTGATNCGGTATTTT

CTCCTTACNCATCTGTNCCGTATTTCCACCGCATATGGTGCACTCTCAATACAATCTGC

TCTGATCCNCATAATTTAANCCANCCCCGAAACCCGCCCAACACCCCTTAAAACNCCCT

TAACGGGCTTGTNTGCTCCCGGCATCCGCTTAACAAANAAACTTTTAAACGTNTCCCGG

AACNGCATNTTTTNAAAGTTTTCACCCNCCTCCC

FIG. 17

(SEQ ID NO:17)

ACATGATTACGCCAAGCTATTAGGTGACACTATANAATACTCAAGCTTATGCATGCGGC

CGCATCTAGAGGGCCCGGATCGCCCTTCCCAACAGTTGCGCAGCCTGAATGGCGAATGG

ACGCGCCCTGTAGCGGCGCATTAAGCGCGGCGGGTGTGGTGGTTACGCNCANCGTGACC

GCTACACTTGCCAGCGCCCTAGCGCCCGCTCCTTTCGCTTTCTTCCCTTCCTTTCTCGC

CACGTTCGCCGGCTTTCCCCGTCAAGCTCTAAATCGGGGGCTCCCTTTAGGGTTCCGAT

TTAGTGCTTTACGGCACCTCNACCCCNAAAAACTTGATTAGGGTGATGGTTCACGTATT

GGGCCATCNCCCTGATAGACAGTTTTTCGCCCNTTGACGTTGGAGTCCACGTTCTTTAA

TATTGGACCTTGTTCCAAACTGGAACAACACTCAACCCTATCTCGGTCTATTCTTTTGA

TTTATAAGGGATTTTGCCNATTTCGGCCNATNGGTTAAAAAATGAGCTNATTTAACNAA

AATTTAACGCGAATTTTAACAAAATATTNAANCTTACAATTTCCTNATGCGGGTATTTT

CTCCTTACNCATCTGTGCGGTATTTTACAACCGCATATGGTGCCTCTCAATTACNANNT

GCTCTGAATGCCGCATATTTTAAACCAACNCNGAAANCCCNTCCAANNACCCNCTTAAN

CGCCCCGAACGGGTTGNTCTGCCCCNGCATCCCTTANNAAACAACTTTTAACCTTCTCC

TGGAACTTCNNTTTTTNAAAGGTTTCCNCCN

FIG. 18

(SEQ ID NO:18)

ACGGNTTNTGAATNGTTATTTAGGTGACACTATAGAAATACTCAAGCTTATGCATGCGG

CCGCATCTAGAGGGCCCGGATCCACCCCGTCTTCCACTGTTCGTTACTACGCGAGCATC

NCGGCCCTCCACCACCCCGACAAGATACTTGGCCATTGGAATTCATAACCCATCAGCCT

GTCCCACGTCCCTTGTGTATTCTGGACTCTAAACTCGACCTCTCATCATCTCCGCCAAA

CAAACTCGTCCTCGTACAGTGGACGGGCCAACCCCCTGAGGATACTACCTGGGAGCCNT

GGTCAGAAATNCCTNACCTTTACCACCTCNAGGACAAGTGGTCCTCNCGGCGACNGTA

TTGATNACNGTTACCCGGAAGATACCCAGATTGAGCCCCCACTTACTAAGACNAAGCCC

AACGTTNCCCCTCNAGACCTGCTTCTTGAATGACTACNANACTGACTCNANGAAGAAGC

TCCAACCATTNGTTNCCNAAGTTATTAGGGTNGTTACCCAATTAGTTTAGAACGTTNTT

CCGTTGAAAAGGCTCATGTTACCCCCCTCNCNNTTTTTTAATNCTTGAATANATNATTA

AGAAGGCCTGCCNNAGGTTACNTTACTCCCTCCCCNCTCTCTANATTTCCTNTANGAAG

CTGCCTTCCCCCNAAATTAGGGGCCATTCTCTTCCTTTCCCGTCTTTTCACTCCCCTCT

GCTCTTATCNNGAATTCNCCTTGATNAACCCCCGGTTTTNGGATANAATTGAATTNAC

CCCCCTTCTTGAAAANAGAAGTTTTTTCN

FIG. 19

(SEQ ID NO:19)

ACGGCAGTGANTGTAATNCGACTCACTATAGGGCGAATTGGCCAAGTCGGCCGAGCTCG

AATTCGTCGACCTCGAGGGATCGCCGAAGTATCGACTCAACTATCAGAGGTAGTTGGCG

TCATCGAGCGCCATCTCGAACCGACGTTGCTGGCCGTACATTTGTACNGCTCCGCNGTG

GATGGCGGCCTGAAGCCACACNGTGATATTGATTTGCTGGTTACNGTGACCGTAAGGCT

TGATGAAACNACGCGGCGAGCTTTGATCCACNATGCCCATNACCNAGAGTAGACCAGAA

TCTAACACNAATCNCATTGTCNGATATAACNAAATGCTTTTTAACACGAGTGCTTCCCC

TNACANTGTTAGATTTGAGCCCANCTCCCTTCTCAATGATACATNCAGGATGAACNNTT

TGACATNNCTCCACCNATTTGGNAGTCTCATGCACCACCACATTCCNCAGTATGTTTG

AAGGTCNTTGGCCNGTTCCCTTANANAAATATTCCTCCGCCNNTTCAGGTTGANTCTCA

TTCCNNAAAATATATCCCCTTGTCCATTTCCATCTNCAATTCNTNCTGTTNGAAAGAAC

NTTTGCTTCCAGCNTTCTTCCCAAANCNATTTTTNGGAAACCCTCTGTTTTCNAAGAAA

TTGGGTTCANCTCCAATTCTNTCCATTCCNAAGGGGTTCCTCCACTTTAACCCCGNATN

ANCAACCAAGGGGAATTGAAAAAACGGGAAAGGGAAAAAAATNGGGCCTACTTNCAAGG

GAANGGCGCCCCCTCAAGNAAATTTNCAAAGAAGNANANAA

FIG. 20

(SEQ ID NO:20)

NGNCGACGCCNGTGNATGACCACTATAGGGCGAATTGGCCAAGTCGGCCGAGCTCGAAT

TCGTCGACCTCGAGGGATCTATATATAGGCTTGCTAAGGGTAGAGAGAGGAAGACTAGA

GATTTGGATCNACAATGCCAATAACAAAGAGTTNACCAGAATCNAACACAAATCNCATT

GTCNGATATAACAAAATGCTTTTTAACACGAGTGCTTCACATAACAGTGTNAGATTTGA

GCCCAACTCCTTTCTCAATGATACATCCNGGATGGACCAATTTGACATGCATCACCNAT

TTGGCAGTCTCATGCACAACCACATTTCCCACANTATGTNTGANGGTCATTGGCCNGTT

CACTAAGANAATTATTCCTCCCCAGTTCANGTNGAGTCTCANTCCNNAAATATAGTCCC

TTTGTCCNATTTCCNTCTNAAATCCTTCCTGTGGAAAGACCATTGCATNCAGCTTTCTA

TCNGAAACAATATTTGGAAACCCCTCTGTCTTCCAAGAAATNGGTGTCCNCTCNATTCT

NTCCCATACCNAAGGGTTCATCCAGTTTACCCTGATTAGANCNNAAGGGAGTGGAAANA

CCGGGAAAGGAANAAAATNGGCCNACTTCCAAGGAAGGCCCCTCCNTNAGAAAATTTTG

AGAGAGAGAGAAGAGTTCCTTNACCTTTGCCTGCCTCNTTATATTANTCCAGTNTTATN

CCCNCNANGGTGGTTACCNAANCCTTTTCCNCCNAATACNGTCTNACTAATTTGGTACT

ACCCCNCCCCTTNGTACCAN

FIG. 21

TABLE OF THE GENETIC CODE

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

FIG.22

METHOD OF DETERMINING SOYBEAN SUDDEN DEATH SYNDROME RESISTANCE IN A SOYBEAN PLANT

PRIORITY APPLICATION INFORMATION

This application is a continuation of U.S. patent application Ser. No. 09/007,119 filed Jan. 14, 1998, now U.S. Pat. No. 6,300,541, which claims priority to U.S. provisional patent application Ser. No. 60/035,335, filed Jan. 14, 1997, both of which are incorporated herein by reference in their entirety.

TECHNICAL FIELD

The present invention relates to soybeans and methods of soybean breeding. More particularly, the invention relates to soybean sudden death syndrome resistant soybean lines and methods of breeding same, the method involving genetic marker analysis; and soybean cyst nematode resistant soybean line and methods of breeding same, the methods involving genetic marker analysis.

The publications and other materials used herein to illuminate the background of the invention, and in particular cases, to provide additional details respecting the practice, are incorporated herein by reference, and for convenience, are referenced by author and date in the following text, and respectively group in the appended list of references.

BACKGROUND OF THE INVENTION

Soybeans are a major cash crop and investment commodity in North America and elsewhere. Soybean oil is one of the most widely used edible oils, and soybeans are used worldwide both in animal feed and in human food production.

Soybean sudden death syndrome (SDS) is a fungal disease of soybean (*Glycine max* (L.) Merr.), caused by *Fusarium solani* (Mart.) Sacc. f. sp. *phaseoli* (Burk.) Snyd. & Hans., type A (Rupe, 1989; Roy et al., 1989, O'Donnell and Gray, 1995). Since its discovery SDS has become one of the most destructive pests in soybean. It has been reported in nearly all states that soybean are grown, and it causes production problems in several states, being particularly destructive in Midwestern states. See generally (Mulrooney 1988, Gibson et al., 1994, Hartman et al., 1995, Wrather et al., 1995, 1996). For example, susceptible soybean cultivars had 5-60% lower yield than did resistant cultivars on *F. solani* infested sites in Illinois (Gibson et al., 1994).

Although the use of fungicides is effective in reducing the population level of the fungus, fungicide use is both uneconomical and environmentally unsound as a control measure in soybean production. Neither is crop rotation a practical means of fungal control since rotation with a non-susceptible crop for at least two years is necessary for reducing soybean losses. Therefore, it has long been felt by soybean breeders that use of resistant varieties is the most practical control measure.

Screening of soybean germplasm for resistance to SDS was begun soon after the discovery of the fungus in the U.S. (Gibson et al., 1994; Rupe et al., 1991). Soybean breeding for resistance to SDS has mostly utilized genes from the cultivar 'Forrest' (Hartwig 1970) and 'Pyramid' (Myers et al., 1980). However, low yield of these cultivars necessitates the introgression of their SDS resistance into elite germplasm with a minimum of linkage drag.

Resistance to SDS is multigenic and quantitative in soybean (Hnetkovsky et al., 1996; Njiti et al., 1996). Chang et al., (1996, 1997) estimated that Forrest has 5 genes required for resistance to SDS. Njiti et al., (1996) and Kilo et al., (1996) estimated that Pyramid has 3 genes required for resistance to SDS, 2 that were different from those in Forrest. The multiple genes and genetic backgrounds involved contribute to the difficulty breeders have in developing SDS resistant soybean varieties.

Breeding programs for SDS resistance rely primarily on field evaluations where fungal populations occur. However, these populations can be mixtures of undetermined amplitypes (Achenbach et al., 1996) and the environment can vary thereby affecting the overwintering and infection capability of the fungus. Although evaluations using single oospore based fungal isolates in controlled greenhouse environments are possible, they are prohibitively expensive and are difficult to manage for larger breeding programs. These deficiencies in each evaluation method made SDS a difficult trait for soybean improvement.

Genetic markers closely linked to important genes may be used to indirectly select for favorable alleles more efficiently than direct phenotypic selection (Lander and Thompson 1990). SDS resistance loci have been associated with RFLP and microsatellite markers and tentatively mapped to linkage groups G (two), N and C1 (from Forrest); to linkage group C2 (from Essex); to linkage groups A2, B and G (from Pyramid) (Hnetkovsky et al., 1996; Chang et al., 1996, 1997; Abu-Thredeih et al., 1996; Kilo et al., 1996; Torto et al., 1996). In addition SDS resistance loci have been associated with the SCN resistance phenotype (Gibson et al., 1994) and soybean cyst nematode (SCN) resistance loci rhg1, rhg3 and Rhg4 on linkage groups G, B, and A2 respectively (Webb et al., 1995; Chang et al., 1996, 1997; Abu-Thredeih et al., 1996; Kilo et al., 1996).

U.S. Pat. No. 5,491,081, issued to Webb with Assignee Pioneer HiBred International, Inc. describes a method for introgressing SCN resistance into soybean germplasm as well as quantitative trait loci associated with SCN. It also describes SCN as a particular problem to soybean breeders and farmers. However, this patent does not discuss soybean SDS.

Therefore, it is of particular importance, both to the soybean breeders and to farmers who grow and sell soybeans as a cash crop, to identify, through genetic mapping, the quantitative trait loci (QTL) for resistance to SDS, and to identify additional QTL for resistance to SCN. Knowing the QTLs associated with resistance to SDS and to SCN, soybean breeders will be better able to breed SDS resistant and SCN resistant soybean that also possess other genotypic and phenotypic characteristics required for commercial soybean lines.

DISCLOSURE OF THE INVENTION

The invention provides a method of introgressing SDS and SCN resistance into non-resistant soybean germplasm. Loci associated with SDS resistance in soybean lines known to be resistant to SDS are used in marker assisted selection during introgression of SDS resistance into elite germplasm. Loci associated with SCN resistance in soybean lines known to be resistant to SCN are used in marker assisted selection during introgression of SCN resistance into elite germplasm. In addition the method may be used to confirm selection of resistance in new soybean cultivars.

The present invention provides a method of introgressing SDS resistance into non-resistant soybean germplasm. Loci associated with SDS resistance in soybean lines known to be SDS resistant are used in marker assisted selection during introgression of SDS resistance into elite soybean germplasm. Examples of soybean germplasm known to be resistant to SDS include Forrest, Pyramid, Essex, Ripley, Jack, Hartwig, PI520.733. PI567507B, PI567.365, PI567.446B and PI567.373B. The method of the present invention can be used to breed soybeans resistant to any SDS causing $F.$ $solani$ strain.

The method of the present invention comprises the use of nucleic acid markers genetically linked to loci associated with SDS resistance in lines known to be resistant to SDS. The markers are used in genetic mapping of genetic material of soybean lines to be used in and/or which have been developed in a breeding program, allowing for marker assisted selection during introgression of SDS resistance into elite germplasm.

According to the method of the invention, any art-recognized genetic mapping techniques can be utilized, with preferred embodiments utilizing Restriction Fragment Length Polymorphism (RFLP) mapping, AFLP mapping, RAPD mapping or microsatellite mapping, using the nucleic acid markers recognized or applicable to the particular method(s). Markers useful in genetic mapping include, for example, the following: For linkage group G, $OI03_{450}$, $OI03_{512}$, SATT309, SATT214, SATT275, SIUSAT122, CTAAGG280, CGGAGA300, ATGCGA190, AGGCAC310, CCACCA120, CCCTC220, ACGCAT80, $OG13_{490}$, Bng122, SATT163 and SATT38; A112I, $OE04_{450}$, $OE02_{1000}$, and SATT130. For linkage group N $OC01_{500}$, $OO04_{1075}$ and SATT9; For linkage group C2, $OO05_{250}$, K455D and $OP13_{500}$; For linkage group B or D, $OG01_{1000}$, $SZ19_{500}$, and SATT71; or linkage group A2, $OW15_{1000}$, AO85, $OA12_{1000}$, BLT65, CCAAGC309, CCCATG349, CCGAAC400, CCGAAC401, CCCATG350, CCAAGC310, OW15500, $OD04_{500}$. For linkage group C1, A063I and SAT40.

An alternative embodiment of the present invention comprises a method of confirming selection for SDS resistance. This embodiment comprises identifying products of a soybean breeding program having in their genetic material the loci associated with resistance to SDS.

A further embodiment of the present invention comprises QTL associated with SDS resistance. Exemplary loci of the invention are mapped (or identified as defined) using particular nucleic acid markers, as discussed above, and are further defined by their association with particular art-recognized linkage groups.

An additional embodiment of the invention comprises soybeans resistant to SDS or to SCN bred according to the method of the present invention, or developed through the identification of parental lines possessing one or more QTL of the invention. Thus, an embodiment of this invention includes soybean plants, seeds and tissue cultures resistant to SDS and to SCN. Further, an embodiment of this invention includes soybean plants, seeds and tissue cultures that include QTL associated with SDS resistance and with SCN resistance.

An additional embodiment of this invention includes the genetic markers associated with SDS resistance and with SCN resistance that are isolatable from soybeans; and which are free from total genomic DNA. Exemplary markers are set forth more fully below, and are characterized by molecular weight and sequence data. The sequences of particular markers are set forth in FIGS. 3-21. Additionally, the sequences of the markers can be derived from the abbreviations of the markers more fully described below, as these abbreviations include standard PCR primer information and molecular weight information. For the markers of this invention, including the sequence of FIGS. 3-21, it is contemplated that the present invention includes DNA segments from such markers and complementary strands of such markers; DNA sequences which hybridize to the markers or segments thereof; and DNA sequences which but for the degeneracy of the genetic code would hybridize to the markers. More particularly, it is contemplated that DNA segments of the markers such as would be useful as probes for hybridization techniques such as northern blots, southern blots, nuclease protection assay and the like; and that DNA fragments of the markers such as would be useful as PCR primers are within the scope of this invention. The markers are used to close resistance genes, which enables the transfer of such genes among elite cultivars by transformation.

As used herein, the term "DNA segment" refers to a DNA molecule which has been isolated free of total genomic DNA of soybeans. Included within the term "DNA segment", are DNA segments and smaller fragments of such segments, and also recombinant vectors, including, for example, plasmids, cosmids, phage, viruses, and the like.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to a particular marker, such as, but not limited to any of those in FIGS. 3-21, such as about 10 nucleotides or 25 nucleotides. DNA segments with total lengths of about 1,000, 500, 200, 100 and about 50 base pairs in length are also contemplated to be useful.

Allowing for the degeneracy of the genetic code, sequences which have between 20% and about 50%; or more preferably, between about 50% and about 70%; or even more preferably, between about 70% and about 99%; of nucleotides which are identical to the nucleotides of FIGS. 3-21 will be sequences which are "essentially as set forth in FIG. 3"; "essentially as set forth in FIG. 4"; "essentially as set forth in FIG. 5"; "essentially as set forth in FIG. 6"; "essentially as set forth in FIG. 7"; "essentially as set forth in FIG. 8"; etc. Sequences which are essentially the same as those set forth in FIGS. 3-21 may also be functionally defined as sequences which are capable of hybridizing to a nucleic acid segment containing the complement of FIGS. 3-21 under relatively stringent conditions. Suitable relatively stringent hybridization conditions will be well known to those of skill in the art (Sambrook et al., 1989, *Molecular Cloning Laboratory Manual, 2d Edition*).

By way of example, nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combinations of parameters is much more important than the measure of any single parameter. (See, e.g., Wetmur & Davidson, 1968; Kanehisa, 1984).

Additionally, now that loci for SDS and SCN resistance have been described herein, it will be apparent to one having ordinary skill in the art that known resistance genes or DNA segments having homology to known resistance genes can be used to identify, confirm and/or screen for SDS or SCN resistance or for loci that confer SDS or SCN resistance. As is known in the art, resistance genes are typically found at common loci on the genome. A probe derived from a known resistance gene is used to prove plant nucleic acids to look for mapping of the probe to the loci for SDS or SCN resistance. Thus, the use of known resistance gene is used to probe plant nucleic acids to look for mapping of the probe to the loci for SDS or SCN resistance. Thus, the use of known resistance genes or DNA segments having homology to known resistance gene to identify, confirm and/or screen for SDS or SCN resistance is contemplated to be within the scope of this invention.

Another embodiment of the invention pertains to an isolated and purified soybean rfs1 gene, said gene capable of conveying *Fusarium solani*-infection resistance to a non-resistant soybean germplasm, said gene located within a quantitative trait locus mapping to linkage group G and mapped by genetic markers $OI03_{512}$ and Bng122, said gene located along said quantitative trait locus between said markers.

Another embodiment of the invention pertains to an isolated and purified soybean rft1 gene, said gene capable of conveying *Fusarium solani* toxin resistance to a non-resistant soybean germplasm, said gene located within a quantitative trait locus mapping to linkage group G and mapped by genetic markers $OI03_{512}$ and SATT309, said gene located along said quantitative trait locus between said markers.

Another embodiment of the invention pertains to a method of determining soybean sudden death syndrome resistance in a soybean plant in a greenhouse setting, the method comprising the steps of inoculating soil with a low density inoculum of *Fusarium solani*; planting a soybean plant in said inoculated soil; growing said plant in said soil for a predetermined period of time in a greenhouse; isolating *Fusarium solani*-infected tissue from said plant; culturing said infected tissue for a period of time sufficient to allow for fungal colony forming unit growth; statistically determining disease severity and/or infection severity in said plant using the number of said fungal colony forming units; and comparing said disease severity and/or said infection severity to disease severity and/or infection severity data from genetic markers associated with soybean sudden death syndrome resistance to identify a correlation, the presence of a statisically signficant correlation indicating the presence of soybean sudden death syndrome resistance in said soybean plant.

Another embodiment of the invention pertains to a method of characterizing resistance to soybean sudden death syndrome in a soybean plant, the method comprising the steps of isolating roots from a soybean plant infected by *Fusarium solani*; culturing the root on a culture plate including a restrictive growth medium that provides for slow fungal growth and restricted bacterial growth; determining root infection severity by statistically evaluating the number of *Fusarium solani* colony forming units on said culture plate; and characterizing resistance to soybean sudden death syndrome in said soybean plant based on said determined root infection severity.

The invention differs from present technology by enabling selection directly on the resistance alleles of gene by linked markers rather than by the phenotype they cause. It solves the problem quickly and cheaply selecting resistant cultivars, assembling many resistance genes in a single cultivar, mixing resistance genes in novel combinations, defining what genes confer resistance in new cultivars and predicting resistance in cultivars. The invention will be used to improve selection for SDS and SCN resistance in soybean. It enhances the process of soybean breeding for increased yield and disease resistance.

Some of the objects and advantages of the invention having been stated hereinabove, other objects and advantages will become evident as the description proceeds, when taken in connection with the accompanying drawings as best described hereinbelow.

BRIEF DESCRIPTION OF THE DRAWINGS

FIG. 1A depicts soybean linkage map from the Essex by Forrest RIL population. The map was generated by the computer program Mapmaker using locus segregation data for flower color, 26 RFLPs, 91 RAPD bands, 10 DAF bands and 3 microsatellites. Loci for which linkage was not detected are not shown unless the locus was identified by an RFLP marker that was mapped with the same enzyme and the same band sizes as in Shoemaker and Specht (1995). These anchored RFLP markers were used to identify linkage groups where possible (eg. A); groups with no such markers were numbered arbitrarily (eg. SIU1); or tentatively in parentheses (eg. SIU4 (D, J or K)). Marker loci are identified by a horizontal bar and a probe designation after Cregan et al., (1995). Two subscipts by a RAPD primer name indicates aparently codominant RAPD loci. The most likely position of A85H and Rhg4 between A112H and K636 was inferred from Webb et al., (1995). Distances are given as Haldane centimorgans cM. END indicates the likely position of the telomeres on linkage groups. Thick vertical bars represent regions of the genome less than 10 cM from the nearest marker. Thin vertical bars represent regions of the genome further than 10 cM from the nearest marker.

FIG. 1B shows locations of four QTL conditioning SDS DI and one conditioning SCN race 3 resistance in Forrest and Essex. The QTL were putatively assigned to linkage group C2, G, and N on the soybean genetic map by anchored RFLP (Shoemaker and Specht, 1995; Concibido et al., 1995) or microsatellite markers (Akkaya et al., 1995). END shows the likely position of the telomere on a linkage group. The thin vertical bar indicates the rest of the linkage group. Marker names are given on the left and marker-QTL LOD scores are given on the right of each linkage group. LOD scores at markers were from single-locus analyses of additive gene effects using MAPMAKER/QTL 1.1. Genetic distances (cM) were from the recombinant inbred line function of MAPMAKER/EXP 3.0. A cM distance scale is shown below in group C2. The estimated position of the QTL is shown based on 2 cM interval mapping using MAPMAKER/QTL 1.1. Boxes indicate the region with greater than 1-LOD (10 fold) likelihood intervals.

FIG. 1C depicts exact positions of the SDS and SCN resistance genes on linkage group G relative to SATT309, Bng122D and $OI03_{512}$. To the left is the LOD plot for the RIL population and the supporting map (Chang et al 1996; 1997); to the right is the map from the NIL populations. Markers names for AFLP markers mapped are shown without band size for clarity. The dark bar indicates the confidence interval for the position of the rhg1 and rft1 genes (LOD>5). The grey bars indicate the confidence intervals for the QTL conditioning resistance to SDS leaf scorch (LOD>4). The white bar indicates the confidence interval for the rfs1 gene conditioning root infection severity (LOD>4). Distances are given in centimorgans ±0.5 cM.

FIG. 1D depicts exact positions of the SDS and SCN resistance Rhg4 genes on linkage group A2 relative to BLT65, CCAAGC309, CCCATG349, CCGAAC400, CCGAAC401, CCCATG350, CCAAGC310 cM and OW15$_{500}$. Distances are given in centimorgans ±0.5 cM.

Figure 2:
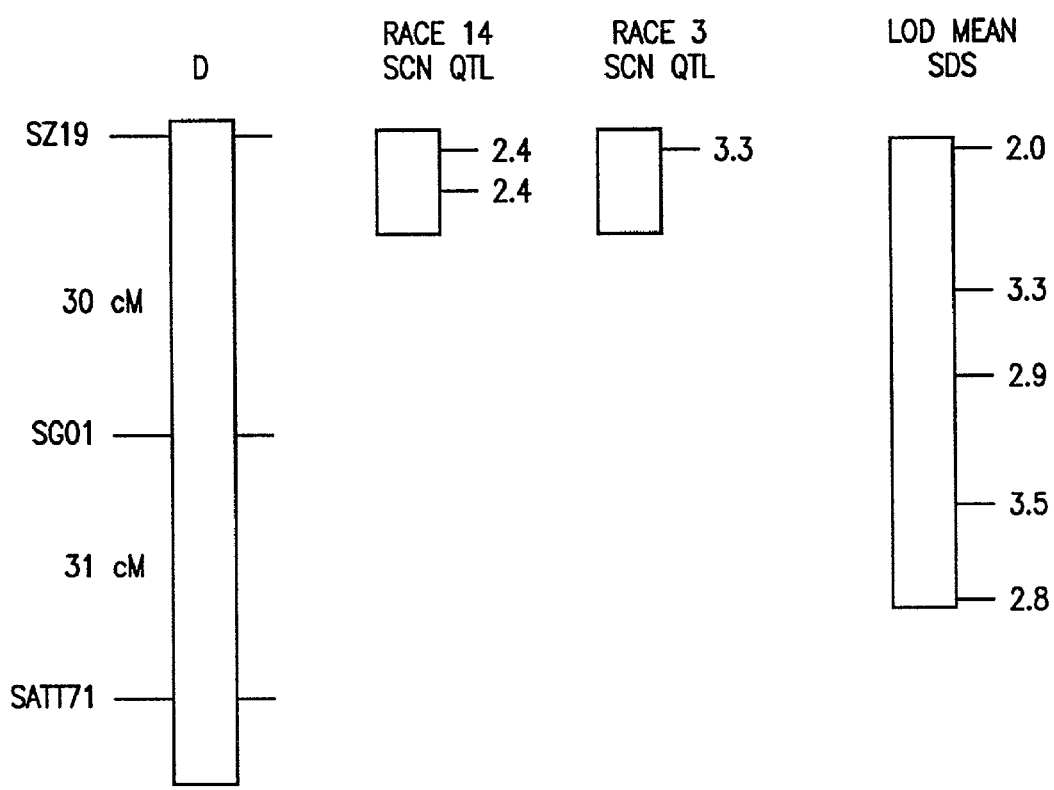

FIG. 2 shows locations of two QTL conditioning SDS DI and SCN race 3 and race 14 resistance in Pyramid. The QTL were putatively assigned to linkage group A2 and B on the soybean genetic map by anchored RFLP (Shoemaker and Specht, 1995; Concibido et al., 1995) or microsatellite markers (Akkaya et al., 1995). END shows the likely position of the telomere on a linkage group. The thin vertical bar indicates the rest of the linkage group. Marker names are given on the left and marker-QTL LOD scores are given on the right of each linkage group. LOD scores at markers were from single-locus analyses of additive gene effects using MAPMAKER/QTL 1.1. Genetic distances (cM) were from the recombinant inbred line function of MAPMAKER/EXP 3.0. A cM distance scale is shown below group D. The estimated position of the QTL is shown based on 2 cM interval mapping using MAPMAKER/QTL 1.1. Boxes indicate the region with greater than 1-LOD (10 fold) likelihood intervals.

FIGS. 3A and 3B set forth DNA sequence data for markers flanking each major SDS and/or SCN resistance loci.

FIG. 4 sets forth DNA sequence data for markers flanking each major SDS and/or SCN resistance loci.

FIG. 5 sets forth DNA sequence data for markers flanking each major SDS and/or SCN resistance loci.

FIG. 6 sets forth DNA sequence data for markers flanking each major SDS and/or SCN resistance loci.

FIG. 7 sets forth DNA sequence data for markers flanking each major SDS and/or SCN resistance loci.

FIG. 8 sets forth DNA sequence data for markers flanking each major SDS and/or SCN resistance loci.

FIG. 9 set forths DNA Sequence data close to Bng122D determined from bacterial artificial chromosomes. Potential microsattelite sequence are included (bold) and primers used to assay the are underlined.

FIG. 10 sets forth DNA sequence data close to Bng122D detrmined from Bacterial artificial chromosomes for markers flanking each major SDS and/or SCN resistance loci.

FIG. 11 sets forth DNA sequence data close to Bng122D detrmined from Bacterial artificial chromosomes for markers flanking each major SDS and/or SCN resistance loci.

FIG. 12 sets forth DNA sequence data close to Bng122D detrmined from Bacterial artificial chromosomes for markers flanking each major SDS and/or SCN resistance loci.

FIG. 13 sets forth DNA sequence data close to Bng122D detrmined from Bacterial artificial chromosomes for markers flanking each major SDS and/or SCN resistance loci.

FIG. 14 sets forth DNA sequence data close to Bng122D detrmined from Bacterial artificial chromosomes for markers flanking each major SDS and/or SCN resistance loci.

FIG. 15 sets forth DNA sequence data close to Bng122D detrmined from Bacterial artificial chromosomes for markers flanking each major SDS and/or SCN resistance loci.

FIG. 16 sets forth DNA sequence data close to Bng122D detrmined from Bacterial artificial chromosomes for markers flanking each major SDS and/or SCN resistance loci.

FIG. 17 sets forth DNA sequence data close to Bng122D detrmined from Bacterial artificial chromosomes for markers flanking each major SDS and/or SCN resistance loci.

FIG. 18 sets forth DNA sequence data close to Bng122D detrmined from Bacterial artificial chromosomes for markers flanking each major SDS and/or SCN resistance loci.

FIG. 19 sets forth DNA sequence data close to Bng122D detrmined from Bacterial artificial chromosomes for markers flanking each major SDS and/or SCN resistance loci.

FIG. 20 sets forth DNA sequence data close to Bng122D detrmined from Bacterial artificial chromosomes for markers flanking each major SDS and/or SCN resistance loci.

FIG. 21 sets forth DNA sequence data close to Bng122D detrmined from Bacterial artificial chromosomes for markers flanking each major SDS and/or SCN resistance loci.

FIG. 22 sets forth a table of the genetic code.

Figure 23:
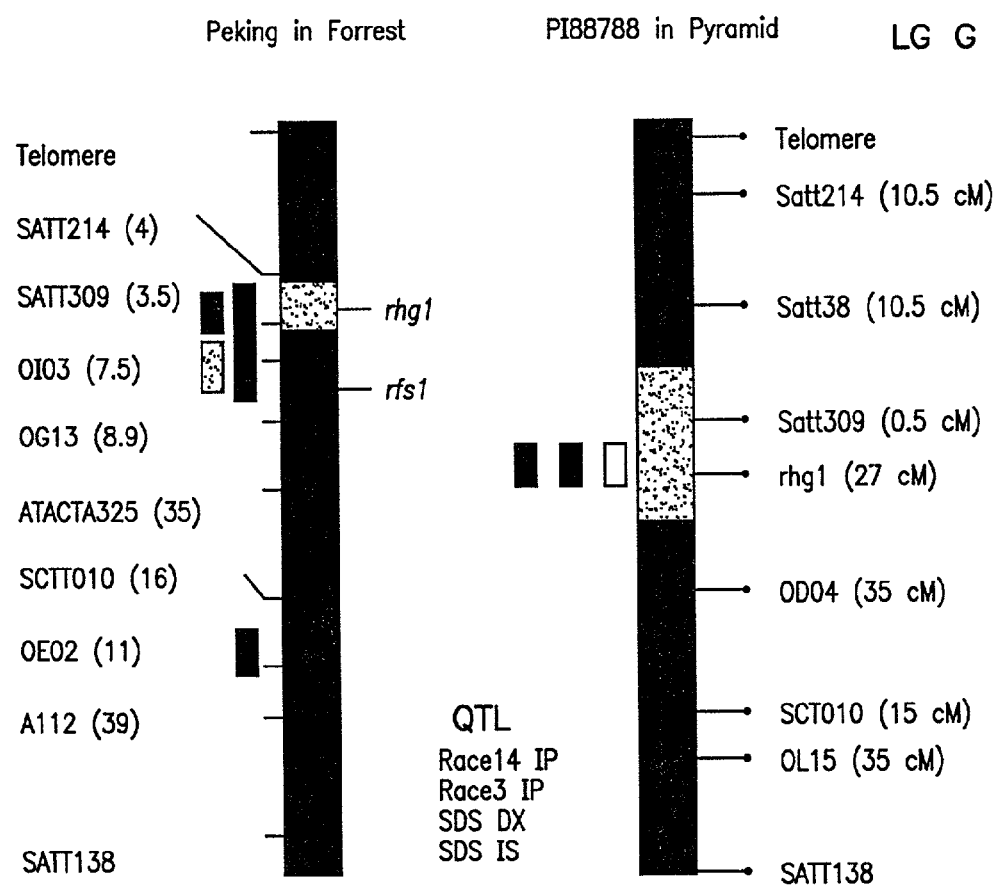

FIG. 23 sets forth a map of linkage group G.

DETAILED DESCRIPTION OF THE INVENTION

Broadly this invention relates to a soybean plant and a method of producing the same, which is resistant to soybean sudden death syndrome (SDS). This invention relates to the introgression in soybean of genetic material (for the first time identified) which is capable of causing the plant to be resistant to soybean sudden death syndrome (SDS). Additionally the present invention relates to method of introgression of the desired genetic material from one or more parent plants into the progeny with precision and accuracy.

This invention also relates to a soybean plant and a method of producing the same, which is resistant to soybean cyst nematodes (SCN). This invention relates to the introgression in soybean of genetic material (for the first time identified) which is capable of causing the plant to be resistant to soybean cyst nematodes (SCN). Additionally the present invention relates to method of introgression of the desired genetic material from one or more parent plants into the progeny with precision and accuracy.

It should be appreciated that the SDS-resistant or SCN-resistant converted line offers a much improved donor for use in pedigree or backcrossing programs because recombination for genes for yield and other desirable agronomic traits have already been accomplished by the present invention. To assist in the description of this invention the following glossary of terms are provided.

"Converted plant" shall mean any plant having resistance to SDS or resistance to SCN and additionally the plant or an ancestor of the plant was or has been selected by reference to RFLP, RADF, AFLP or microsatellite data for at least one of the loci herein defined.

"Cross-over" shall mean an exchange of segments of homologous chromosomes during meiosis whereby linked genes become recombined; also the product of such an exchange. The cross-over frequency is the proportion of gametes bearing a cross-over between two specific gene loci. It generally ranges from 0 for allelic genes to 50% for genes so far apart that there is always a cross-over between them. The cross-over site is the place in the chromosome where breakage and reunion of DNA strands occur during recombination.

"Introgression" shall mean the entry or introduction of a gene or a quantitative trait loci from one plant into another.

"Introgressing" shall mean entering or introducing a gene or a quantitative trait loci from one plant into another.

"Linkage block" or "linkage group" shall mean an identified chromosomal region containing genetic material that expresses a desired trait.

"Quantitative trait locus" shall mean a genomic region including a gene underlying a trait on which many genes act.

"Recombination" shall mean reassortment of genes or characters in combinations different from what they were in the parents, in the case of linked genes by crossing over.

"An improved soybean plant, and parts thereof" as used herein and in the claims shall mean an entire soybean plant; all parts thereof, including but not limited to seeds, leaves, stems and roots; and soybean plant tissue cultures.

Nucleic acid sequences which are "complementary" are those which are capable of base-pairing according to the standard Watson-Crick complementarity rules. That is, that the larger purines will always base pair with the smaller pyrimidines to form only combinations of Guanine paired with Cytosine (G:C) and Adenine paired with either Thymine (A:T) in the case of DNA or Adenine paired with Uracil (A:U) in the case of RNA.

"Hybridization techniques" refer to molecular biological techniques which involve the binding or hybridization of a probe to complementary sequences in a polynucleotide. Included among these techniques are northern blot analysis, southern blot analysis, nuclease protection assay, etc.

"Hybridization" and "binding" in the context of probes and denatured DNA are used interchangeably. Probes which are hybridized or bound to denatured DNA are aggregated to complementary sequences in the polynucleotide. Whether or not a particular probe remains aggregated with the polynucleotide depends on the degree of complementarity, the length of the probe, and the stringency of the binding conditions. The higher the stringency, the higher must be the degree of complementarity and/or the longer the probe.

"Probe" refers to an oligonucleotide or short fragment of DNA designed to be sufficiently complementary to a sequence in a denatured nucleic acid to be probed and to be bound under selected stringency conditions.

"Detectable moiety" refers to a modification to the probe nucleic acid that enables the experimenter to identify the labeled nucleic acid in the presence of unlabeled nucleic acid. Most commonly, this is the replacement of one or more atoms with radioactive isotopes. However, other detectable moieties include covalently attached chromophores, fluorescent moieties, enzymes, antigens, groups with specific reactivity, chemiluminescent moieties, and electrochemically detectable moieties, etc.

"PCR technique" describes a method of gene amplification which involves sequenced-based hybridization of primers to specific genes within a DNA sample (or library) and subsequent amplification involving multiple rounds of annealing, elongation and denaturation using a heat-stable DNA polymerase.

"RT-PCR" is an abbreviation for reverse transcriptase-polymerase chair reaction. Subjecting mRNA to the reverse transcriptase enzyme results in the production of cDNA which is complementary to the base sequences of the mRNA. Large amounts of selected cDNA can then be produced by means of the polymerase chain reaction which relies on the action of heat-stable DNA polymerase produced by *Thermus aguaticus* for its amplification action.

"Nuclease protection assay" refers to a method of RNA quantitation which employs strand specific nucleases to identify specific RNAs by detection of duplexes.

"In situ hybridization of RNA" refers to the use of labeled DNA probes employed in conjunction with histological sections on which RNA is present and with which the labeled probe can hybridize allowing an investigator to visualize the location of the specific RNA within the cell.

"Cloning" describes separation and isolation of genes.

"Sequencing" describes the determination of the specific order of nucleic acids in a gene or polynucleotide.

The term "homology" describes a mathematically based comparison of sequence similarities which is used to identify genes or proteins with similar functions or motifs.

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e., nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

The present invention relates to a novel and useful method for introgressing, in a reliable and predictable manner, SDS resistance into non-resistant soybean germplasm. The method involves the genetic mapping of loci associated with SDS resistance. SDS resistance can be determined in any acceptable manner.

The soybean line selected for mapping is subjected to DNA extraction (Hnetkovsky et al., 1996). Nucleic acid probes are used as markers in mapping the resistance loci, and appropriate probes are selected based upon the mapping method to be used. The probes can be either DNA or RNA probes and mapping is performed using RFLP, RAPD, AFLP, SCAR or microsatellite technology.

In a particular embodiment, DNA probes are used for RFLP, RAPD, AFLP, microsatellite, or SCAR markers. Such probes come from, for example, PstI-cloned genomic libraries, and the cloned inserts used as probes may be amplified, for example by PCR, LCR, NASBA™, microsatellite amplification using specific primers, SCAR sequence amplification using specific primers, AFLP amplification from EcoRI-MseI digested DNA, or other amplification methods recognized in the art. For example the markers useful in a preferred embodiment of the invention include the following: For linkage group G, $OI03_{450}$, (particularly useful in RAPD) $OI03_{512}$ (RAPD), SATT309 (microsatellite), SATT214 (microsatellite), SATT275 (microsatellite), SIU-SAT122 (microsatellite), CTAAGG280 (AFLP), CGGAGA300 (AFLP), ATGCGA190 (AFLP), AGGCAC310 (AFLP), CCACCA120 (AFLP), CCCTC220 (AFLP), ACGCAT80 (AFLP), $OG13_{490}$ (RAPD), Bng122 (RFLP), SATT163 (microsatellite) and SATT38 (microsatellite), A112I (RFLP), $OE04_{450}$ (RAPD), $OE02_{1000}$ (RAPD), and SATT130 (microsatellite). For linkage group N, $OC01_{500}$ (RAPD), $OO04_{1075}$ (RAPD), and SATT9 (microsatellite). For linkage group C2, $OO05_{250}$ (RAPD), K455D (RFLP) and $OP13_{500}$ (RAPD), For linkage group B or D, OG01$_{1000}$ (RAPD), SZ19$_{500}$ (RAPD), and SATT71 (microsatellite); or linkage group A2, OW15$_{1000}$ (RAPD), AO85 (RFLP), OA12$_{1000}$ (RAPD), BLT65 (RFLP and SCAR), CCAAGC309 (AFLP), CCCATG349 (AFLP), CCGAAC400 (AFLP), CCGAAC401 (AFLP), CCCATG350 (AFLP), CCAAGC310 (AFLP), OW15$_{500}$ (RAPD), and OD04$_{500}$ (RAPD). For linkage group C1, A063I (RFLP) and SAT40. of course, it will be apparent to those skilled in the art that other markers that map to loci for SDS resistance may be utilized in the practice of the invention. For RFLP mapping, restriction fragments are generated using specific restriction enzymes, and the digestion, electrophoresis, Southern transfers and nucleic acid hybridizations are conducted according to art recognized techniques. See, e.g., Keim et al., (1989) the disclosures of which are hereby incorporated herein by reference.

In an alternative embodiment of the method of the invention, RAPD technology can be utilized for genetic mapping. A DNA preparation is amplified using art-recognized amplification techniques, and suitable nucleic acid markers are used; for example: For linkage group G, OI03$_{450}$, OI03$_{512}$, OG13$_{490}$, OE04$_{450}$ and OE02$_{1000}$. For linkage group N, OC01$_{500}$ and OO04$_{1075}$; For linkage group C2, OO05$_{250}$, and OP13$_{500}$; For linkage group D, OG01$_{1000}$ and SZ19$_{500}$; for linkage group A2, OW15$_{1000}$ and OA12$_{1000}$.

In a soybean breeding program, the method of the present invention envisions the use of marker assisted selection for one or more loci at any stage of population development in a two parent population, multiple parent population, or a backcross population. Such populations are well-known in the art and are described in Fehr W. R. 1987, *Breeding Methods for Cultivar Development*, in J. R. Wilcox (ed.) *Soybeans: Improvement Production and Uses,* 2d ed., the disclosures of which are hereby incorporated herein by reference.

Marker-assisted selection according to art-recognized methods may be made, for example, step wise, whereby the different SDS resistance loci are selected in more than one generation; or, as an alternative example, simultaneously, whereby all five loci are selected in the same generation. Marker assisted selection for SDS resistance may be done before, in conjunction with, or after testing and selection for other traits such as seed yield. Marker-assisted selection is generally described in the following U.S. Pat. Nos. 5,536, 901, 5,612,191, 5,606,823, 5,574,210, 5,492,547, 5,491,081, 5,476,524, and 5,385,835, the entire contents of each of which are herein incorporated by reference.

The DNA from target populations may be obtained from any plant part, and each DNA sample may represent the genotype of single or multiple plant individuals (including seed).

Marker assisted selection may also be used to confirm previous selection for SDS resistance or susceptibility made by challenging plant with *F. solani* in the field or greenhouse and scoring the resulting phenotypes.

The following examples are offered by way of illustration and not by way of limitation.

EXAMPLE 1

Identification of SDS Resistance Loci in Forrest and Essex

Materials and Methods

Plant Material

The 'Essex' by 'Forrest' (E×F)F$_5$ derived population of soybean recombinant inbred lines (RILs) was constructed by crossing Essex (Smith and Camper, 1973) and Forrest (Hartwig and Epps, 1973). Essex is SDS susceptible, while Forrest is SDS resistant (FIG. 1B; Gibson et al., 1994). About 4500 F$_2$ plants were inbred to the F$_5$ generation using a single pod descent method. In year one, a random bulk of seed was planted to obtain 500 F$_5$ plants of which 150 were randomly selected, only intentionally excluding a few agronomically undesirable extremes. In year two, 100 F$_5$-derived lines of modal maturity (mid-maturity group V) with sufficient seeds for field testing were retained. All inbreeding occurred in fields with minimal incidence of soybean cyst nematode (SCN) and no history of SDS.

SDS Disease Scoring

Eight field experiments were conducted over a four year period encompassing a total of eight locations in southern Illinois, of these useful data could be derived from five locations. The other three were excluded due to poor stand and absent or minimal SDS leaf symptoms resulting from drought. The five were Villa Ridge Year One (V Year One); Cora Year Two (C Year Two); Pulaski Year Two (P Year Two); Cora Year Three (C Year Three); and Ridgway Year Four (R Year Four) (C Year Two and C Year Three were separate fields, 2 km apart). All fields were selected based on a history of visually uniform SDS infestation and managed as described by Gibson et al., (1994).

The 100 E×F F$_5$ derived lines were scored for disease intensity (DI), disease severity (DS) and yield as described (Gibson et al., 1994). Two row plots in a partially balanced simple 11×11 lattice design (2 replications, 8 duplications per parent and 5 checks) were used. Disease was rated weekly and the last score before and the first score after R6 (full pod) were used to standardize DI and DS to the R6 stage. DI was defined as the percentage of plants in the plot with visible leaf symptoms. DS was rated as the degree of leaf damage on diseased plants and was scored on a scale of 1 to 9 (1=0-10%/1-5%, 2=10-20%/6-10%, 3=20-40%/10-20%, 4=40-60%/20-40%, 5=>60%/40% chlorosis/necrosis whereas 6=1-33%, 7=34-66%, 8=66-100% premature defoliation and 9=premature death) (Gibson et al., 1994). Yield was determined at harvest from the two row plots trimmed to 3 m (4.3 m planted). There was no intra-plot bordering since the progeny population displayed uniform growth habit and maturity dates. Lattice adjusted means were used whenever the lattice analysis was more efficient than the RCB. To detect transgressive segregants, an LSD (P=0.05) for across environment means of individual lines vs. parents was calculated using the genotype×environment interaction as the error variance.

SCN Score Determination

The methods for SCN scoring of the E×F lines have been described in detail (Matthews et al., 1991; Njiti et al., 1996). Briefly, the lines were characterized for their resistance to SCN race 3 in the greenhouse by their reaction in soil containing a field population of *H.glycines* collected from Elkville, Ill. in Year One. The race characterization of the soil was based on SCN disease reactions of standard differentials compared with Essex (Rao-Arelli and Anand, 1988). The pots were placed on top of a heating pad to regulate temperature, the temperature in the soil ranged from 20° to 23° C. The index of parasitism (IP) of each F$_{5:7}$ derived line was calculated from the average cyst count of six single-plant replications compared to Essex, 36 days after planting. Using six plant replications allowed the detection of segregation in lines with residual heterogeneity in genomic regions encompassing SCN resistance genes. Lines with a mean IP greater than 8 and less than 25 compared to Essex were screened again but with 18 single plant replications. The group with resistance to SCN (Table 1) was defined as those lines with IP less than 10 (SCN score<1.0). The group of lines defined as susceptible to SCN showed an IP of 10 or greater (SCN score ≧ 1.0). Lines segregating for resistance to SCN were identified by equal numbers of plants within the line with contrasting Ips. SCN IP was converted to a SCN score on a 0-5 scale to ease scoring and reduce within genotype variability associated with the assay method and the unselected field SCN population used. SCN score was defined as 0=0 IP; 1=1-10 IP; 2=11-20 IP; 3=21-60 IP; 4=61-100 IP; 5>100 IP. Trait data were used for QTL analysis both directly (Concibido et al., 1994; Webb et al., 1995) and after being partially normalized by square root transformation.

DNA Clones

Bacterial strains containing cloned soybean PstI genomic DNA inserts were obtained from Dr. R. Shoemaker, USDA ARS, Ames, Iowa (Shoemaker and Specht, 1995).

Plant DNA Extraction, Restriction Digestion, Electrophoresis and Southern Transfers Leaf material for DNA extraction was collected from 20 $F_{5:9}$ field grown plants per genotype in July 1992 (Agronomy Research Center, Southern Illinois University at Carbondale) and frozen (-70° C.).

DNA extraction from leaf tissue was modified for legumes (Hnetkovsky et al., 1996). Aliquots of soybean DNA were digested with one of five restriction enzymes: TaqI, DraI, EcoRI, EcoRV, or HindIII based on informative probe enzyme combinations. DNA fragments were resolved by gel electrophoresis on a 10 g $L^{-1}$ agarose gel, then transferred and fixed to Hybond-N+ (Amersham Corporation, Arlington Heights, Ill.)

The informative probe-enzyme combinations were generated in this study. In total 243 RFLP probes were tested for the ability to detect polymorphism between Essex and Forrest. Polymorphic RFLP loci were referred to using the naming convention suggested by the Soybean Genetics Committee (Soybean Genetics Newsletter, 1995, 22:11-22).

DNA Hybridizations

Plasmid DNA was digested with PstI and inserts were purified by gel electrophoresis and elution for use in radio-labeling reactions as described by Hnetkovsky et al., (1996). Briefly, 50 to 100 ng of probe DNA was labeled with $^{32}$P-dCTP by random hexamer primed synthesis. Hybridization was performed according to techniques described in Hnetkovsky et al., (1996).

RAPD Protocol-Polymerase Chain Reaction

The amplification reactions were performed after Williams et al., (1990) with 180 separate primers from kits A, B, C, D, E, F, G, H and O from Operon Technologies (Almeda, Calif.). The total volume of 25 ml contained 100 mM DATP, dCTP, dGTP, and dTTP, 0.2 mM of a 10 base pair primer, 10-40 ng genomic DNA, and either 1.0 unit taq polymerase with 1.5 mM $MgCl_2$ (Promega, Madison, Wis.; Perkin Elmer Cetus, Norwalk, Conn.) or 2.5 units of the Stoffel fragment of Taq polymerase with 3 mM $MgCl_2$. DNA was amplified in a thermal cycle (Savant, New York, N.Y.) programmed for 45 cycles of 1 minute at 94° C., 1 minute at 36° C., and 2 minutes at 72° C. Amplification products were analyzed by electrophoresis on a 14 g $L^{-1}$ agarose gel stained with ethidium bromide. Primers which generated distinct polymorphic bands between Essex and Forrest across a range of soybean DNA concentration (10-40 ng) were identified and used to amplify DNA samples from the $F_{5:9}$ lines to generate segregation data for mapping analysis. RAPD markers amplified with Taq polymerase reported here were $OC01_{650}$ and $OF01_{1000}$. All others were amplified by Stoffel fragment polymerase. RAPD markers associated with SDS resistance were amplified independently on three or more separate occasions to assure reproducibility. Polymorphic RAPD loci were referred to using the naming convention suggested by the Soybean Genetics Committee (Soybean Genetics Newsletter, 1995, 22:11-22).

Mapping Quantitative Resistance Level

To discover genomic regions associated with SDS resistance the RILs were classified as Essex type or Forrest type (heterozygotes were excluded) for each marker and compared with SDS disease response scores by analysis of variance (ANOVA). One-way ANOVA was performed with SAS (SAS Institute Inc., Cary, N.C.). The probability of association of each marker with each trait was determined and a significant association was declared if $P \leq 0.005$ (unless noted otherwise in the text) to minimize the detection of false associations (Lander and Botstein, 1989). Mapmaker-EXP 3.0 (Landers et al., 1987) was used to calculate map distances (cM) between linked markers using the RIL (ri-self) genetic model. To identify intervals containing QTL governing SDS response the marker map and disease data were simultaneously analyzed with Mapmaker/QTL 1.1 (Paterson et al., 1988) using the $F_2$-backcross model for trait segregation (Webb et al., 1995). Putative QTL were inferred with LOD ($\log_{10}$ of odds ratio) scores exceeded 2.0 at some point in each interval.

Heritability

The broad sense heritability determination of 0.89 for DI indicated the number of plants showing SDS leaf symptoms within inbred lines was highly consistent. With heritability high, non-genetic variation was well controlled and genetic loci contributing to phenotypic variation could be more accurately detected with markers.

Locations of Four SDS Resistance Loci

Four independent marker loci had P values less than 0.005 and LOD scores greater than 2.0 for association with SDS resistance. These markers were located on linkage groups C2, G (two loci) and N (Table 2, FIG. 1). Approximate map position for resistance QTL were estimated based on approximate the size of the marker QTL score and the distances between the markers.

Ten of the 100 lines had greater SDS resistance (a mean DI lower) than Forrest. Eight of these lines were significantly transgressive when the LSD was determined from the genotype×environment of the subset of the 10 lines numerically superior to Forrest and excluding data from Forrest. The smaller $LSD_{05}$ (4.8) involved in this comparison reflects the consistently low DI scores of these lines in all environments. The eight transgressive lines may be useful starting points for developing soybean cultivars with stronger SDS resistance. Six resistant lines were expected in this inbred population provided 4 genes were needed and had normal 1:1 segregation ratios which is not significantly different from the eight to ten found. One resistant line is to be released to soybean breeders as a germplasm release under the Plant Variety Protection Act (Schmidt et al. 1998).

Lines having resistance marker type on C2, G (both loci) and N were more resistant to SDS than Forrest (Table 3). Both this and the allele trait values for the locus on linkage group C2 showed that resistance to SDS was partly contributed by Essex.

EXAMPLE 2

Identification of an SDS Resistance Locus in Forrest in the Greenhouse

Materials and Methods

*Fusarium solani* strain ST90, maintained on 5× Bilays medium at 19 C, was transferred onto PDA plates at 28 C for inoculum preparation. The 40 E×F RILs used were the 20 most resistant to SDS in the field and the 20 most susceptible to SDS in the field.

Infested Seed Assay

Plants were inoculated employing the infested oat technique (Stephens et al., 1993). Oats were soaked in tap water overnight, then excess water was strained away. The 150 ml portions were put into 250 ml Erlenmeyer flasks, capped, and autoclaved for 20 minutes. Oats were then cooled and three 1 cm² agar plugs from the colony borders of *F. solani* petri plates were aseptically added to the sterilized oats. The inoculated oats were incubated in the dark at room temperature (24 C) for three weeks. Flasks were constantly shaken for uniform growth. Plants were grown in a soil medium containing a 1:1 (v/v) mixture of sterilized sand and sterilized soil taken from Ridgway. Inoculation of the plants was done at v2-v3 stage of growth by placing five infested oats next to the taproot below the soil surface. Plants were then irrigated to seal the soil, and soil was kept saturated to ensure the pathogenicity of the fungus.

Cornmeal Sand Assay

The cornmeal method of inoculation was used with a few modifications. Two 1 cm×1 cm square pieces of the infested agar was transferred into a 50 ml volume of cornmeal and silica mix (1:1) and moistened with sterile water. This was kept in an incubator for 14 days. At the same time seeds were sown on steamed sand. After 14 days, the inoculum was mixed with steamed sand/soil (1:1 v/v) in a 1:40 proportion. Styrofoam cups were filled and 14 day old seedlings were transferred into the filled cups. These were set in water filled basins with enough water to keep them moist. The experimental design was a 2-factor randomized complete block with treatment as a split on genotype. After 21 days, disease severity based on a scale of 1-9 (1=plants with no leaf chlorosis and 9=dead plant) was scored. Other trait data were root weight, shoot weight and plant height. Data analysis used a one-way analysis of variance (ANOVA).

Greenhouse Traits

There was a high significant difference between treatments for E×F and the RILs (Table 1). This significant dry root weight and shoot weight confirm the pathogenicity of the strain of *Fusarium solani* used and the effectiveness of the assays as a whole. As seen on the same table, there was significance among the lines for all the traits measured except disease severity. The frequency distribution of disease severity for the E×F RILs was normal (P>0.16) not bimodal. The field scores and greenhouse scores were not significantly correlated for either assay.

Marker Associations

One marker was associated with the resistance to SDS trait measured for the forty lines tested in the cornmeal sand assay (Table 4). A063I on linkage group C1 was associated with SDS resistance measured by DS. The beneficial allele was from Forrest. Additional analysis using the extreme twenty lines of E×F (10 best and 10 worst for field SDS score) showed $OR10_{380}$ and $OR10_{400}$ on linkage group SIU1 was associated with SDS resistance measured by DS. The beneficial allele was from Forrest.

TABLE 1

Means of disease incidence (DI) and disease severity (DS) of 100 $F_5$ derived lines from the cross Essex by Forrest

|  | n | DI (%) | DS (1-9) |
|---|---|---|---|
| Essex | 8 | 58.9 | 1.6 |
| Forrest | 8 | 16.5 | 1.2 |
| Progeny | 100 | 48.5 (23) ≠ | 1.5 (0.3) |
| h (%) |  | 90 | 78 |

≠ Standard deviation among progeny line means is shown in parentheses.

TABLE 4

Probabilities of F for variance among lines and treatments

| Source | df | DS | RWT | SHWT | HT |
|---|---|---|---|---|---|
| LINE | 41 | ns | 0.001 | 0.03 | 0.05 |
| TREAT | 1 | 0.001 | 0.001 | 0.001 | 0.001 |

DS - Disease Severity. RWT - Dry root weight. SHWT - Dry Shoot Weight. Ht - Height

TABLE 2

Intervals most likely to contain the SDS QTL that show significant associations with mean SDS disease incidence across five locations

| QTL No. DNA Marker | and Linkage group† | $R^2$ | P > F | LOD≠ | QTL var.§ | Mean DI % for RILs with alleles from | |
|---|---|---|---|---|---|---|---|
|  |  |  |  |  |  | Essex | Forrest |
| $OG13_{490}$ | 1G | 0.17 | 0.0001 | 4.0 | 17.0 | 57.8 ± 3.2 | 38.5 ± 2.9 |
| $OI13_{450}$ | 1G | 0.20 | 0.0001 | 5.1 | 20.0 | 60.2 ± 3.2 | 39.6 ± 3.1 |
| $OE04_{450}$ | 2G | 0.16 | 0.0011 | 3.1 | 17.4 | 54.1 ± 3.9 | 37.6 ± 3.2 |
| $OE02_{1000}$ | 2G | 0.10 | 0.0097 | 3.7 | 14.3 | 48.8 ± 3.6 | 37.2 ± 2.3 |
| $OO05_{250}$ | 1C2 | 0.13 | 0.004 | 2.3 | 11.1 | 35.7 ± 3.5 | 52.5 ± 3.1 |
| K455D-1 | 1C2 | 0.16 | 0.0005 | 2.9 | 15.4 | 40.4 ± 4.4 | 61.3 ± 3.4 |
| $OC01_{650}$ | 1N | 0.16 | 0.001 | 1.8 | 10.7 | 71.3 ± 2.4 | 49.5 ± 3.8 |
| $OF04_{1600}$ | 1N | 0.10 | 0.009 | 1.3 | 8.0 | 55.7 ± 3.8 | 41.4 ± 3.5 |

†C2, G and N were assigned from Soybase, based on Shoemaker and Specht (1995), the SDS QTL were numbered arbitrarily.
≠LOD is the $\log_{10}$ of the odds ratio that supports evidence for the presence of the QTL at the locus from Mapmaker/QTL 1.1.
§the percent variation associated with the interval from Mapmaker/QTL 1.1.

TABLE 3

Marker genotypes and SDS DI means of RILs with the most resistant and least resistant phenotypes based on entry means over five locations

| | | | Linkage Group† | | | | | | | |
|---|---|---|---|---|---|---|---|---|---|---|
| | SDS | Yield | A | | C | | G | | N | |
| Line | DI | kg ha$^{-1}$ | G13≠ | I03 | O05 | K455 | E04 | E02 | C01 | F04 | GS§ |
| 78* | 4.4 | 4120 | − | + | − | + | − | + | + | − | 3.5 |
| 59 | 7.2 | 3870 | + | + | + | − | + | + | + | + | 7.0 |
| 37 | 7.8 | 3850 | + | + | + | + | + | + | + | + | 7.5 |
| 44 | 8.2 | 3760 | + | + | + | − | + | + | + | + | 6.5 |
| 57 | 8.8 | 3890 | + | + | + | + | + | + | + | + | 7.5 |
| 23 | 8.9 | 3960 | + | + | + | + | − | + | + | + | 7.0 |
| 67 | 9.8 | 3920 | + | + | + | + | + | − | + | + | 6.5 |
| 47 | 10.6 | 3715 | + | + | + | + | − | − | + | − | 5.0 |
| Forrest | 16.5 | 3760 | + | + | − | − | + | + | + | + | 6.0 |
| Essex | 58.9 | 3330 | − | − | + | + | − | − | − | − | 2.0 |

†from Soybase, based on Shoemaker and Olson (1993).
≠Presence of the beneficial allele at the marker is +absence is − and heterogenous or not scored unequivocally is o
§Genotypic score is the sum of individual loci base on + = 1, o = 0.5 and − = 0.
* Genotype to be released under the Plant Variety Protection Act

TABLE 5

Marker association with traits in the cornmeal sand assay using the extreme 40 ExF lines for field SDS.

| | | | | | ALLELIC MEANS | |
|---|---|---|---|---|---|---|
| MARKER | LG | TRAIT | P | R$_2$ | E | F |
| A063 | C1 | DS | 0.028 | 0.429 | 5.0 | 3.0 |

DS - Disease Severity. RWT - Dry root weight. SHWT - Dry Shoot Weight. HT - Height

TABLE 6

Markers showing significant association with field disease parameters as well as greenhouse traits

| | | | | | | ALLELIC MEANS | |
|---|---|---|---|---|---|---|---|
| MARKER | LG | P (field) | TRAIT | P | R$^2$ | E | F |
| a, Cornmeal Assay | | | | | | | |
| OR10$_{380}$ | SIU1 | 0.036 | DS | 0.010 | 0.440 | 3.4 | 5.1 |
| OR10$_{400}$ | SIU1 | 0.036 | DS | 0.010 | 0.440 | 3.4 | 5.1 |

DS - Disease Severity. RWT - Dry root weight. SHWT - Dry Shoot Weight. HT - Height

EXAMPLE 3

Identification of Two SDS Resistance Genes Close to a SCN Resistance Gene in Forrest Materials and Methods Plant Material The cross of 'Essex' (Smith and Camper, 1973) by 'Forrest' (Hartwig and Epps, 1973) (E×F) was made and an F$_5$ derived population of 100 RILs generated. During the studies described herein the RILs were advanced to the F$_{5:13}$ generation from never less than 300 plants per generation. Essex is susceptible to both SDS and SCN, while Forrest is resistant to both SDS and SCN race 3 (Gibson et al. 1994; Hnetkovsky et al. 1996). The potential for unintentional natural selection for resistance to SDS or resistance to SCN was reduced by all inbreeding being carried out in fields with low incidences of soybean cyst nematodes (SCN) and no history of SDS symptoms.

Residual heterogeneity within RILs, theoretically 6.25%, was about 8% as detected by codominant markers at the F$_{5:9}$ (Hnetkovsky et al. 1996; Chang et al. 1996). For the RFLP marker Bng122D six RILs that were heterogeneic were detected. Two of these RILs E×F11 and E×F34 were used to extract subline populations of 40 individuals at the F$_{5:9}$ generation by seed to row descent (Njiti et al. 1997b). Subline populations from the F$_{5:9:11}$ to F$_{5:9:13}$ were used to test for resistance to SDS and SCN.

Assays of Resistance to SDS

The soybean NILs, Essex and Forrest were planted in a randomized complete block design in two row plots, three replications, and four Southern Illinois locations (Villa Ridge Year One (v Year One), Ridgway Year Two (R Year Two), Ullin Year Two (U Year Two), and Ridgway Year Three (R Year Three)). The Ridgway, soil type was Bonnie silt loam, fine-silty mix, acid, mesic Typic Fluvaquents; Villa Ridge soil type was Belknap Silt Loam, coarse-silty, mixed, acid, mesic typic fluquavents, and Ullin soil type was Patton silty-clay loam, fine-silty mix, mesic, Typic Haplaquolls. Experiments were planted between May 15 and June 15 each year. Rows were 0.75 m wide and 3.0 m long, with about 17 plants/m. At Ridgway Year Three we assayed *F. solani* infection severity (IS) but DX was too low (Essex DX<2.0) to distinguish resistant and susceptible cultivars or NILs. At V Year One, U Year Two and R Year Two we assayed DX where SDS was moderate to severe (Essex DX was 3.0-12; Njiti et al. 1997b).

SDS Disease Scoring

The methods for SDS scoring of the E×F lines have been described in detail (Njiti et al. 1996, Matthews et al. 1991; Hnetkovsky et al. 1996). Three field experiments were conducted during two years in southern Illinois. All fields were selected based on a history of visually uniform SDS incidences. Disease was rated weekly and the last score before and the first score after R6 (full pod) were used to standardize DI (0-100%) and DS (1-9) to the R6 stage. The disease index (DX, 0-100) was calculated as DI.DS/9.

Root Colonization by *F. solani*

The sample was taken at the R8 (harvest maturity) (Fehr et al. 1971) from Ridgway in Year Three. Following Njiti et al. 1997) five plants per plot were randomly harvested, recovering at least 15 cm of the taproot. Roots from sampled plants were transported on ice to the laboratory where they were stored at 4° C. (1 to 7d) until they were processed for *F. solani* isolation and quantification.

Based on the finding by Rupe (1989) that the epidermal tissue of the taproot had the highest frequency of *F. solani* recovery, the isolation in this study was limited to the taproot. A restrictive medium was used that limited fungal growth and restricted bacterial growth (Njiti et al. 1997). The plates were incubated at room temperature for 14 days. Pure colonies of all slow growing fungi from each segment were transferred onto fresh medium, consisting of 24 g/l of PDA and agar, 10 ml/l of 10% NP-10 and 0.064 g/l of tetracycline. The plates were allowed to incubate at room temperature for 14 days.

The percentage of plants yielding blue *F. solani* from at least one segment was determined as infection frequency (IF). The percentage of segments yielding blue *F. solani* from all sampled plants of each plot were determined as infection severity (IS).

SCN Index of Parasitism (IP) Determination

Two SCN indexes of parasitism were determined for each population by comparing the number of white female cysts on each genotype to the number of white female cysts on a susceptible check (Rao-Arelli and Anand, 1988). The first index of parasitism (IP1) was determined at Southern Illinois University at Carbondale using a heterogeneous field population of *H. glycines*, with Essex as the susceptible check. While the second index of parasitism (IP2) was determined at the University of Missouri research center by inoculating the genotypes with 2000±25 eggs from a homogenous isolate of *H. glycines*, with 'Hutcheson, (Rao-Arelli, 1994) as the susceptible check. All experiments were done using five single-plant replications per NIL. The mean number of white female cysts on each genotype and the susceptible check were also determined and IP was the ratio of the mean number of cysts on each genotype to the mean number of cysts on the susceptible check.

RFLP Markers

Bacterial strains containing cloned soybean PstI genomic DNA inserts were obtained from Dr. R. Shoemaker, USDA ARS, Ames, Iowa (Shoemaker and Specht, 1995). Polymorphic loci were detected and screened as described by Chang et al. (1996). Polymorphic RFLP loci were referred to after Cregan et al. (1995).

AFLP Markers

AFLP markers were generated from EcoRI MseI digested genomic DNA exactly as described by Vos et al 1996. AFLP markers are represented by the two selective trinucleotides.

Microsatellite Markers

Microsatellite markers were generated and scored by 6% denaturing PAGE exactly as described by Akkaya et al. (1995). All markers used in this study were Bellsville Agricultural Research Center (BARC) markers. Unless otherwise stated all microsatellite markers described within this application are BARC markers.

RAPD Protocol-Polymerase Chain Reaction

The amplification reactions were done after Williams et al. (1990). DNA was amplified as described previously (Hnetkovsky et al. 1996; Chang et al. 1996).

Mapping Resistance Loci

To detect genomic regions associated with SCN IP and resistance to SDS, the RILs were classified as Essex type or Forrest type for each marker. Markers were compared with SDS disease response scores by the F-test in analysis of variance (ANOVA) done with SAS (SAS Institute Inc., Cary, N.C., 1988). The probability of association of each marker with each trait was determined and a significant association was declared if $P \leq 0.05$ (unless noted otherwise in the text) since the detection of false associations is reduced in isogenic lines (Lander and Botstein, 1989; Patterson et al. 1990).

Selected pairs of markers were analyzed by the two-way ANOVA using the general linear model (PROC GLM) procedure to detect non-additive interactions between the unlinked QTL (Chang et al. 1996; 1997) or Epistat (Chase et al. 1997). Non additive interactions between markers which were significantly associated with SDS response were excluded when $P \geq 0.05$. Selected groups of markers were analyzed by multi-way ANOVA to estimate joint heritabilities for traits associated with multiple QTL. Joint heritability was determined from the $R^2$ term for the joint model in multi-way ANOVA.

Mapmaker-EXP 3.0 (Lander et al. 1987) was used to calculate map distances (cM, Haldane units) between linked markers and to construct a linkage map including traits as genes. The RIL (ri-self) and $F_3$ self genetic models were used. The $\log_{10}$ of the odds ratio (LOD) for grouping markers was set at 2.0, maximum distance was 30 cM. Conflicts were resolved in favor of the highest LOD score after checking the raw data for errors. Marker order within groups was determined by comparing the likelihood of many map orders. A maximum likelihood map was computed with error detection. Trait data were used for QTL analysis (Webb et al. 1995; Chang et al. 1997).

Mean Comparison

The data were subjected to ANOVA (SAS Institute Inc., Cary, N.C.), with mean separation by LSD (Gomez and Gomez 1984). Graphs were constructed by Quattro Pro version 5.0 (Novell Inc., Orem, Utah).

Results

The genomic region identified by the RFLP marker Bng122D, was associated ($0.0004 \leq P \leq 0.006$) with mean SDS DX and IS, accounting for about 16-38% of DX and 38-73% of IS variability (Table 7-8; FIG. 1B). Bng122D was only marginally associated with resistance to SCN. However, the linked (4.3-7.4 cM) microsattelite marker SATT309 was strongly associated with resistance to SCN ($0.0001 \leq P \leq 0.0003$) and explained 24-97% of the variability. SATT309 was also strongly associated with mean DX ($0.0001 \leq P \leq 0.0003$, 25-63% variability) but not IS. Many heterogeneous (11) and recombinant (17) NILs were detected in the populations (n=80) indicating the region contained a locus that selects against fixation (Table 9 and 10). The recombinant NILs among markers and traits enabled fine-mapping of QTL for resistance to SDS and SCN as qualitative loci (FIG. 1B). Our data showed that resistance to SDS DX, SDS IS and SCN IP in Forrest is caused by a two to four gene cluster with close linkage or pleiotrophy between pairs of genes conditioning SDS IS and DX and between SCN IP and SDS DX.

TABLE 7

Markers associated with disease resistance in the ExF34 derived near isogenic line population

| | | | | | Marker | | | | | | | |
|---|---|---|---|---|---|---|---|---|---|---|---|---|
| | Bng122D | | | | OIO3$_{450}$ | | | | SATT309 | | | |
| Trait | P | $R^2$ | | Allele ± SE | P | $R^2$ | | Allele ± SEM | P | $R^2$ | | Allele ± SEM |
| SCN IP1[a] | 0.050 | 23% | E | 0.44 ± 0.19 | 0.006 | 30% | E | 0.55 ± 0.12 | 0.0001 | 42% | E | 0.44 + 0.06 |
| | | | F | 0.19 ± 0.18 | | | F | 0.24 ± 0.11 | | | F | 0.16 + 0.05 |
| SCN IP2[b] | 0.073 | 19% | E | 0.89 ± 0.14 | 0.0001 | 47% | E | 1.10 ± 0.06 | 0.0001 | 97% | E | 0.51 + 0.03 |
| | | | F | 0.44 ± 0.19 | | | F | 0.37 ± 0.14 | | | F | 0.02 + 0.02 |
| VYr1DX[c] | 0.046 | 23% | E | 8.5 ± 1.40 | 0.014 | 21% | E | 9.5 ± 0.98 | 0.0005 | 49% | E | 9.66 + 0.92 |
| | | | F | 4.5 ± 0.98 | | | F | 5.90 ± 0.95 | | | F | 3.99 + 0.93 |
| UYr2DX | 0.003 | 38% | E | 8.0 ± 2.05 | 0.001 | 35% | E | 8.73 ± 1.67 | 0.002 | 41% | E | 7.01 + 1.48 |
| | | | F | 0.8 ± 0.18 | | | F | 2.03 ± 0.83 | | | F | 0.91 + 0.42 |
| RYr2DX | 0.008 | 36% | E | 27.9 ± 4.17 | 0.0006 | 37% | E | 31.2 ± 2.84 | 0.0001 | 62% | E | 30.11 + 2.45 |
| | | | F | 12.2 ± 2.54 | | | F | 16.9 ± 2.33 | | | F | 10.92 + 2.42 |
| MeanDX | 0.006 | 38% | E | 14.8 ± 2.36 | 0.0004 | 38% | E | 16.5 ± 1.63 | 0.0001 | 63% | E | 15.65 + 1.37 |
| | | | F | 5.7 ± 1.12 | | | F | 8.29 ± 1.29 | | | F | 5.28 + 1.15 |
| IS (RYr3) | 0.0004 | 73% | E | 56.3 ± 5.1 | 0.0017 | 47% | E | 51.0 ± 4.3 | 0.0797 | 8% | E | 48.43 + 4.93 |
| | | | F | 20.9 ± 4.5 | | | F | 26.± 4.9 | | | | | |

[a] SCN IP1 = SCN index of parasitism, measured in the greenhouse in SIUC and was based on the number of cysts on susceptible check, Essex.
[b] SCN IP2 was calculated in the same manner as IP1 except that the data was collected after infection with SCN eggs at the University of Missouri research station compared to Hutcheson.
[c] Ryr1, Ridgway Year 1; Uyr2, Ullin Year2; RYr2, Ridgeway Year 2. Disease index at R6 stage; DX is DI*DS/9. IS is infection severity by F. solani. E is the allele derived from Essex, F is the allele derived from Forrest.

TABLE 8

Markers associated with Disease resistance in ExF11 sub-lines derived near isogenic line population

| | | | | | Marker | | | | | | | |
|---|---|---|---|---|---|---|---|---|---|---|---|---|
| | Bng122D | | | | OIO3$_{450}$ | | | | SATT309 | | | |
| Trait | P | $R^2$ | | Allele ± SEM | P | $R^2$ | | Allele ± SEM | P | $R^2$ | | Allele ± SEM |
| SCN IP1[a] | 0.42 | 3% | E | 0.40 ± 0.04 | 0.12 | 6% | E | 0.42 ± 0.20 | 0.003 | 24% | E | 0.63 ± 0.24 |
| | | | F | 0.24 ± 0.10 | | | F | 0.20 ± 0.05 | | | F | 0.14 ± 0.02 |
| SCN IP2[b] | 0.02 | 19% | E | 0.60 ± 0.12 | 0.003 | 21% | E | 0.62 ± 0.10 | 0.002 | 25% | E | 63 ± 12 |
| | | | F | 0.21 ± 0.11 | | | F | 0.17 ± 0.09 | | | F | 17 ± 11 |
| VYr1DX[c] | 0.03 | 28% | E | 6.68 ± 1.06 | 0.21 | 9% | E | 5.56 ± 0.94 | 0.09 | 17% | E | 5.92 ± 1.07 |
| | | | F | 3.43 ± 0.86 | | | F | 3.69 ± 0.98 | | | F | 3.28 ± 0.91 |
| UYr2DX | 0.046 | 16% | E | 2.19 ± 0.86 | 0.24 | 4% | E | 1.77 ± 0.59 | 0.03 | 14% | E | 2.70 ± 1.01 |
| | | | F | 0.41 ± 0.19 | | | F | 0.94 ± 0.40 | | | F | 0.80 ± 0.35 |
| RYr2DX | 0.002 | 34% | E | 9.58 ± 1.60 | 0.11 | 7% | E | 7.57 ± 1.24 | 0.003 | 27% | E | 9.47 ± 1.34 |
| | | | F | 3.76 ± 0.72 | | | F | 4.95 ± 1.02 | | | F | 4.20 ± 0.85 |
| Mean DX | 0.002 | 32% | E | 5.91 ± 0.98 | 0.09 | 7% | E | 4.75 ± 0.77 | 0.002 | 25% | E | 6.11 ± 0.97 |
| | | | F | 2.34 ± 0.42 | | | F | 3.04 ± 0.60 | | | F | 2.64 ± 0.53 |
| Mean IS | 0.0039 | 38% | E | 43.2 ± 6.40 | 0.0017 | 39% | E | 42.9 ± 5.60 | 0.183 | 9% | E | 35.6 ± 7.6 |
| | | | F | 21.1 ± 1.80 | | | F | 21.3 ± 3.20 | | | F | 25.2 ± 3.4 |

[a] SCN IP1 = SCN index of parasitism, measured in the greenhouse in SIUC and was based on the number of cysts on the susceptible check, Essex.
[b] SCN IP2 was calculated in the same manner as IP1 except that the data was collected after infection with SCN eggs at the University of Missouri research station compared to Hutcheson.
[c] RYr1, Ridgway Year One; UYr2, Ullin Year Two; RYr2, Ridgeway Year Two. Disease index at R6 stage; DX is DI*DS/9. IS is infection severity by F.solani. E is the allele derived from Essex, F is the allele derived from Forrest.

TABLE 9

Substitution mapping among recombinant lines among ExF 34 derived population either resistant or susceptible based on marker and disease scores.

| Line | SATT309 | SCN[a] | | SDS[b] | | OI03 $_{512}$ | F. solani[b] | | Bng122D |
|---|---|---|---|---|---|---|---|---|---|
| no. | Allele | IP_1/IP_2 | Allele | Allele | DX | Allele | IS | Allelle | Allele |
| 3 | H | 0.23/0.81 | E | E | 24.8 | E | 56 | E | E |
| 9 | E | 0.77/1.08 | E | E | 14.6 | F | 31 | F | F |
| 13 | H | 0.31/0.56 | H | E | 10.3 | E | nd | nd | E |
| 17 | E | 0.48/1.10 | E | E | 19.5 | F | 30 | F | F |
| 19 | H | 0.34/0.28 | H | E | 15.4 | F | 19 | F | E |
| 23 | F | 0.00/0.02 | F | F | 1.4 | F | 60 | E | E |

TABLE 9-continued

Substitution mapping among recombinant lines among ExF 34 derived population either resistant or susceptible based on marker and disease scores.

| Line no. | SATT309 Allele | SCN[a] IP_1/IP_2 | Allele | SDS[b] Allele | DX | OI03$_{512}$ Allele | F. solani[b] IS | Allele | Bng122D Allele |
|---|---|---|---|---|---|---|---|---|---|
| 26 | H | 0.11/0.72 | H | F | 5.9 | F | 53 | E | F |
| 28 | E | 0.50/1.38 | E | E | 11.5 | F | 36 | F | F |

[a]An SCN IP1 of less than 0.23 and more than 0.46 were the critical scores used to distinguish between resistant and susceptible lines. An SCN IP2 of less than 0.03 and more than 0.1 were the critical scores used to distinguish between resistant and suseptible lines. Hetergeneous lines (H) were identified by idividual plants within a line being resistant or susceptible.
[b]A DX of 5.9 or less and 10.3 or more were the critical values used to distinguish between resistant and susceptible lines for disease for disease index.
[c]Infection severity of 36 or less and 54 or more were the critical values used to distinguish between NILs resistant and susceptible to F. solani.

TABLE 10

Sustitution mapping among recombinant lines among ExF 11 derived population either resistant or susceptible based on marker and disease scores.

| Line no. | SATT309 Allele | SCN[a] IP_1/IP_2 | Allele | SDS[b] DX | Allele | OI03$_{512}$ Allele | F. solani[b] IS | Allele | Bng122D Allele |
|---|---|---|---|---|---|---|---|---|---|
| 17 | F | 0.11/0.01 | F | 1.9 | F | E | nd | nd | H |
| 14 | E | 0.38/0.26 | H | 4.1 | E | F | nd | nd | H |
| 33 | F | 0.03/0.45 | H | 3.7 | E | F | nd | nd | H |
| 28 | F | 0.18/0.01 | F | 4.5 | E | F | nd | nd | H |
| 36 | F | 0.18/0.00 | F | 1.2 | F | F | 22 | F | H |
| 3 | H | 0.08/0.02 | F | 1.6 | F | F | nd | nd | H |
| 1 | F | 0.08/0.01 | F | 5.9 | E | F | 50 | E | E |
| 5 | F | 0.18/0.75 | E | 4.9 | E | F | 12 | F | E |
| 35 | F | 0.35/1.09 | E | 2.6 | E | F | 10 | F | E |
| 39 | E | 1.11/0.92 | E | 4.1 | E | E | 23 | F | F |
| 13 | F | 0.26/0.01 | F | 5.3 | E | F | 29 | F | F |
| 19 | E | 0.45/0.68 | E | 2.6 | E | E | nd | nd | F |
| 18 | E | 0.30/1.06 | E | 4.0 | E | E | nd | nd | F |
| 15 | F | 0.10/0.02 | F | 3.0 | E | E | nd | nd | F |
| 10 | F | 0.07/0.00 | F | 1.5 | F | F | 55 | E | E |
| 16 | F | 0.11/0.01 | F | 0.9 | F | E | 56 | E | E |
| 4 | E | 0.37/0.60 | H | 5.6 | E | E | nd | nd | E |

[a]An SCN IP1 of less than 0.23 and more than 0.46 were the critical scores used to distinguish between resistant and susceptible lines. An SCN IP2 of less than 0.03 and more than 0.1 were the critical scores used to distinguish between resistant and susceptible lines. Heterogeneous lines (H) were identified by individual plants within a line being resistant or susceptible.
[b]A DX of 1.9 or less and 2.6 or more were the critical values used to distinguish between resistant and susceptible lines for disease index.
[c]Infection severity of 29 or less and 50 or more were the critical values used to distinguish between NILs resistant and susceptible to F. solani.

EXAMPLE 4

Identification of SDS Resistance Loci in Pyramid Close to SCN Race 3 Resistance Loci Materials and Methods Identical to Examples 1 and 3 with the following exceptions.

Plant Material

The Pyramid by Douglas (P×D) F6 derived population of soybean recombinant inbred lines (RILs) is a typical "South by North" cross. Douglas is SDS and SCN susceptible and Pyramid is SDS, SCN race 3 and SCN race 14 resistant. SCN race 14 resistance derives from PI88.788. SSR Protocol-Polymerase Chain Reaction (PCR):

Amplifications were performed in a Perkin-Elmer 9600V is thermal cycler after Akkaya et al., (1995). Primers were gifts from Dr. Cregan, USDA-ARS, Beltsville, Md. or purchased from Research Genetics.

Results

Heritability

The broad sense heritability determination of 0.8 for DI indicated the number of plants showing SDS leaf symptoms within inbred lines was highly consistent. With heritability high non-genetic variation was well controlled and genetic loci contributing to phenotypic variation could be more accurately detected with markers.

Locations of Four SDS Resistance Loci

Three independent marker loci had P values less than 0.005 and LOD scores greater than 2.0 for association with both SDS resistance and SCN resistance. These markers were located on linkage groups A2, G and D (Table 11, Table 12, FIGS. 2 and 23). We estimated the approximate map position for resistance QTL based on approximate the size of the marker QTL score and the distances between markers.

Gene Pyramiding or Stacking.

The results presented in FIG. 23 (Table 11) show that the SCN resistance genes on linkage groups A2, D and G appear to operate interchangeably. These results imply the genes are functionally the same as one another and that gene product interaction is required for action.

TABLE 11

Markers showing significant (P > 0.005) associations with mean SCN score from Forrest and Pyramid

| DNA Marker | Linkage group† | $R^2$ | P > F | QTL LOD≠ | var.§ | SCN score for RILs with allelas from Essex | SCN score for RILs with allelas from Forrest |
|---|---|---|---|---|---|---|---|
| a, Forrest | | | | | | | |
| OG13$_{490}$ | G | 0.04 | 0.056 | 0.9 | 4.2 | 3.4 ± 0.2 | 2.7 ± 0.3 |
| OI03$_{450}$ | G | 0.14 | 0.0001 | 2.6 | 12.9 | 3.8 ± 0.2 | 2.5 ± 0.3 |
| OW15$_{400}$ | A2 | 0.16 | 0.0001 | 2.4 | 15.1 | 3.9 ± 0.2 | 2.3 ± 0.3 |
| BLT65 | A2 | 0.24 | 0.0001 | 6.1 | 25.2 | 4.2 ± 0.2 | 2.0 ± 0.3 |

| DNA Marker | Linkage group† | $R^2$ | P>F | QTL LOD≠ | var.§ | SCN score for RILs with alleles from Douglas | SCN score for RILs with alleles from Pyramid |
|---|---|---|---|---|---|---|---|
| b, Pyramid | | | | | | | |
| OA12$_{1000}$ | A2 | 0.17 | 0.0004 | 3.1 | 20.0 | 1.6 ± 0.2 | 1.1 ± 0.5 |
| A85H | A2 | 0.09 | 0.0099 | 2.0 | 9.1 | 2.3 ± 0.2 | 1.7 ± 0.3 |
| OG01$_{390}$ | D | 0.14 | 0.0051 | 1.2 | 14.3 | 1.6 ± 0.3 | 1.1 ± 0.4 |
| SATT71 | D | 0.01 | 0.4 | 0.3 | 1.1 | 1.7 ± 0.2 | 1.5 ± 0.3 |
| SATT38 | G | 0.17 | 0.0005 | 3.8 | 17.0 | 1.7 ± 0.2 | 1.3 ± 0.2 |
| OD04$_{950}$ | G | 0.09 | 0.0097 | 1.0 | 10.0 | 2.0 ± 0.2 | 2.9 ± 0.3 |

†G was assigned from Concibido et al., (1995; 1996), based on Shoemaker and Specht (1995). Siu-8 was an anonymous group with no anchored RFLP markers. ? was a single marker not linked to any other locus scored to date.
≠LOD is the $\log_{10}$ of the odds ratio that supports evidence for the presence of the QTL at the locus from Mapmaker/QTL 1.1. nd is not determined because no flanking marker was available.
§the percent variation associated with the interval from Mapmaker/QTL 1.1. nd is not determined because no flanking marker was available.

TABLE 12

Intervals most likely to contain SDS QTL from Pyramid that show significant associations with mean SDS disease index across five locations.

| DNA Marker | Linkage group† | $R^2$ | P > F | QTL LOD‡ | var.§ | Mean DI % for RILs with alleles from Douglas | Mean DI % for RILs with alleles from Pyramid |
|---|---|---|---|---|---|---|---|
| Blt65 | A2 | 0.16 | 0.009 | 2.0 | 16.0 | 53.4 ± 15 | 37.6 ± 14 |
| A85H | A2 | 0.11 | 0.0099 | 2.0 | 9.1 | 52.3 ± 12 | 41.7 ± 10 |
| OG01$_{390}$ | D | 0.14 | 0.0051 | 2.9 | 14.3 | 51.6 ± 13 | 31.1 ± 10 |
| SZ19 | D | 0.01 | 0.006 | 2.0 | 11.1 | 51.7 ± 12 | 33.5 ± 10 |
| SATT38 | G | 0.17 | 0.0005 | 3.8 | 17.0 | 51.7 ± 12 | 31.3 ± 10 |
| SATT3O9 | G | 0.24 | 0.0001 | 4.4 | 25.0 | 55.5 ± 12 | 29.5 ± 10 |
| OD04$_{950}$ | G | 0.09 | 0.0097 | 1.0 | 10.0 | 52.0 ± 12 | 39 ± 13 |

†D, G and A2 were assigned from Soybase, based on Shoemaker and Specht (1995), the SDS QTL were numbered arbitrarily.
‡LOD is the $\log_{10}$ of the odds ratio that supports evidence for the presence of the QTL at the locus from Mapmaker/QTL 1.1.
§the percent variation associated with the interval from Mapmaker/QTL 1.1.

TABLE 13

| MARKER | TRAITS | P | n | $R^2$ | MEAN DI % Allele Pyramid | MEAN DI % Allele Douglas |
|---|---|---|---|---|---|---|
| SP17$_{650}$ | R6DI-Pyr1 | 0.0122 | 87 | 0.0716 | 41.9 ± 23.2 | 40.8 ± 29.1 |
| A85H | R6DI-RYr5 | 0.0057 | 33 | 0.2215 | 13.1 ± 20 | 19.1 ± 7.2 |
| | R6DI-CYr2 | 0.05 | 31 | 0.1154 | 34.3 ± 5 | 56.1 ± 28 |
| | R6DIO-4 | 0.02 | 31 | 0.155 | 51.5 ± 6 | 1.9 ± 5.1 |
| | R6DIO-5 | 0.02 | 24 | 0.1571 | 52.8 ± 16.8 | 50.3 ± 17.3 |

TABLE 13-continued

| MARKER | TRAITS | P | n | $R^2$ | MEAN DI % Allele | |
|---|---|---|---|---|---|---|
| | | | | | Pyramid | Douglas |
| SM11$_{1000}$ | R6DI-CYr1 | 0.0577 | 82 | 0.0442 | 39.7 ± 11.9 | 42.0 ± 8.2 |
| SA02$_{800}$ | R6DI-PYr1 | 0.0122 | 87 | 0.0716 | 41.9 ± 23.2 | 40.8 ± 29.1 |
| SG01$_{390}$ | R6DI-RYr5 | 0.0040 | 84 | 0.0965 | 20.3 ± 17.2 | 21.3 ± 3.7 |
| | R6DI-PYr1 | 0.02 | 90 | 0.0568 | 43.9 ± 28.4 | 32.4 ± 13.8 |
| ST16$_{500}$ | R6DI-CYr1 | 0.0294 | 30 | 0.1584 | 30.4 ± 3.7 | 51.3 ± 14.2 |
| SY13$_{1000}$ | R6DI-CYr2 | 0.0114 | 38 | 0.1650 | 48.0 ± 25 | 33.3 ± 14 |
| | R6DIO-4 | 0.02 | 93 | 0.1251 | 54.0 ± 18.3 | 54.1 ± 11 |
| SY01$_{700}$ | R6DI-CYr1 | 0.0577 | 82 | 0.0442 | 40.0 ± 12.0 | 42.0 ± 8.2 |
| SP08 | R6DI-PYr1 | 0.0018 | 88 | 0.1079 | 44.5 ± 28.1 | 37.7 ± 23.6 |
| SX03$_{1000}$ | RGDI-CYr1 | 0.0216 | 88 | 0.0598 | 37.0 ± 6.9 | 45.3 ± 23.6 |

†CYr1, Cora Year One; PYr1, Pulaski Year One; CYr2, Cora Year 2; RYr3, Ridgway Year 3; RYr5, Ridgway Year Five; O-4 four environment; O-5 five environment mean.

EXAMPLE 5

DNA Markers Derived by Sequence Analysis

Materials and Methods

Figure 1C:
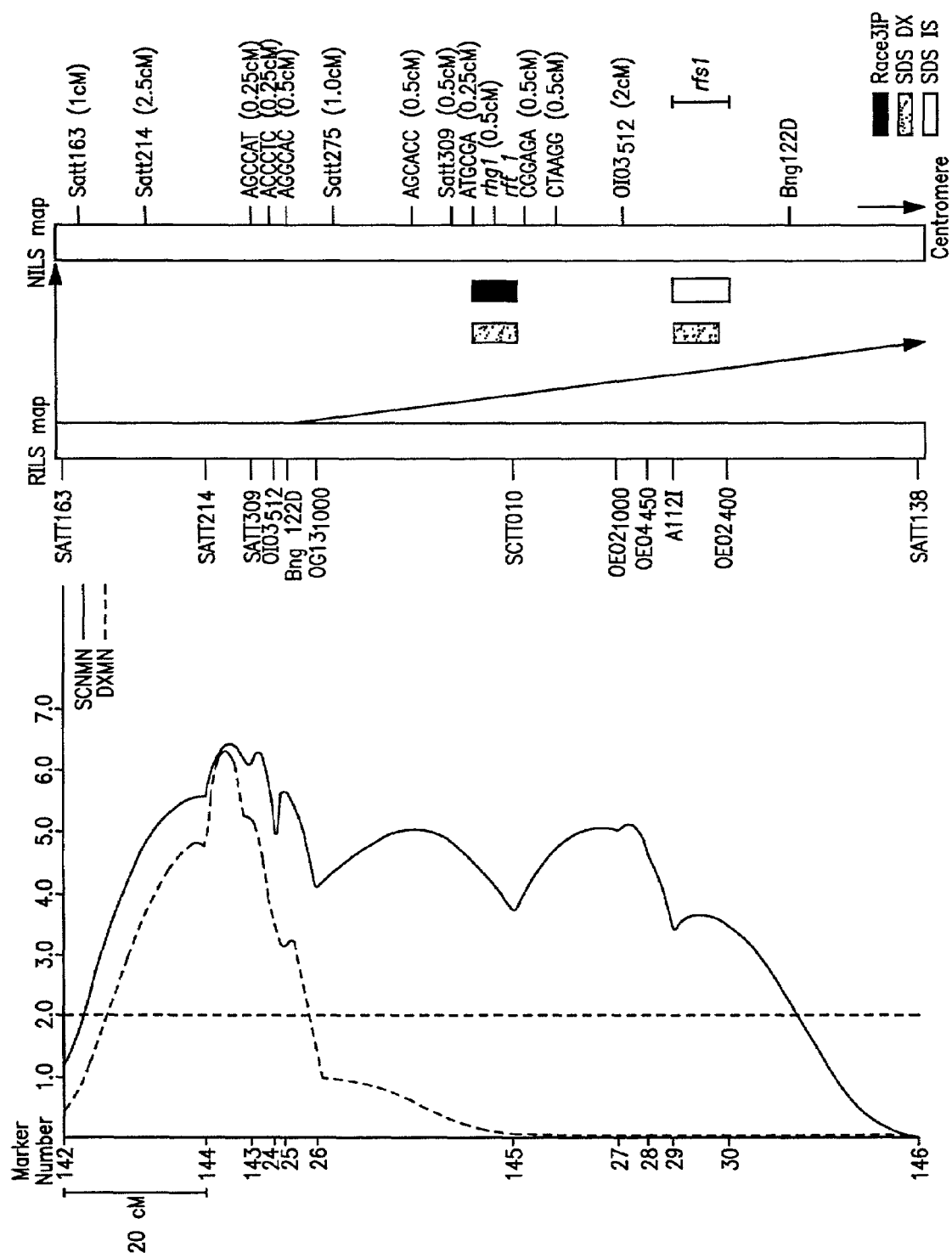

DNA bands, such as bands presented in FIGS. 1 and 2, are excised from gels and cloned into plasmids or sequenced directly according to well-known techniques.

Fingerprinting World Soybean Germplasm:

DNA sequence data for markers flanking each major SDS and SCN resistance loci are shown in FIGS. 3-21. This sequence data is used directly for isolating and determining linked sequences by plasmid, cosmid, BAC or YAC cloning. Polymorphisms among SDS and SCN resistant Pis and cultivars and susceptible cultivars are sought. Comparisons to genetic relationships inferred from RFLP and SSR polymorphism data are made. Selection of material for inclusion in breeding programs is thereby improved.

Developing Breeder Friendly Markers:

From the sequence data found in FIGS. 3-21, and from the other markers identified herein, primer pairs, as for example, PCR primer pairs, capable of distinguishing differences among these genotypes are developed. Simple assays for the markers and genes uses a label, such as, but not limited to, a covalently attached chromophores, that do not need electrophoresis are developed to increase the capacity of marker assisted selection to help plant breeders. Non-destructive sampling of dried seed for DNA preparations are developed to allow selection prior to planting. This enables the testing of the effectiveness of marker assisted selection in predicting field resistance to SDS and SCN.

Additionally, now that loci for SDS and SCN resistance have been described herein, it will be apparent to one having ordinary skill in the art that known resistance genes or DNA segments having homology to known resistance genes can be used to identify, confirm and/or screen for SDS or SCN resistance or for loci that confer SDS or SCN resistance. As is known in the art, resistance genes are typically found on at common loci on the genome. A probe derived from a known resistance gene is used to probe plant nucleic acids to look for mapping of the probe to the loci for SDS or SCN resistance. The probe is prepared and mapping is observed using hybridization techniques as described herein and as are known in the art. Thus, fingerprinting world soybean germplasm and developing breeder friendly markers, as described above, are facilitated using known resistance genes or DNA segments having homology to known resistance genes.

EXAMPLE 6

Soybean Resistant to SDS Selected in Tissue Culture

Materials and Methods

G. max L. seeds used to start cultures should be less than six months old and have been stored in darkness at 4° C. Then, the seeds are cultured as folllows:

1. Surface disinfect with 70% (v/v) ethanol for 2 min then 20% (v/v) bleach for 20 min. Rinse three times in sterile MS media.

2. Germinate the seed on MS media containing 10 g/l agar, 30 g/l sucrose but no PGRs for 3 d at 27° C.

3. Axenically remove the testa, remove the cotyledonary notes, cut the cotyledons transversely in half and use the distal cotyledonary halves to establish callus cultures.

Callus Initiation

Cotyledonary halves are placed on MS medium with 30 g/l sucrose, 5 mM kinetin, 100 mg/l myoinositol, 0.5 mg/mL thiamine.HCl pH 5.7 at 27° C. unless noted below. The medium contains 5 mM indolebutyric acid as auxin. Place cotyledonary halves in tubes containing 10 mL solidified media. Incubate for 28 d.

Callus Growth Assay

Pieces of callus each approximately 25 mg should be added to sterile tubes containing 10 mL media with varying concentrations of F. solani or extracts thereof. After 28 d at 28° C. the explants are evaluated for growth and growing sectors subcultured.

Suspension Cell Bioassay

Cell suspensions are derived by placing 2 g of a macerated callus in 40 mL of MS medium. The flask, a 125 mL Erlenmeyer flask, should be capped with a foam plug. Subcultures should be made every 14 days into fresh media by allowing the cells to settle, removing the old media by aspiration, adding twice the volume of fresh media and splitting into two flasks.

Soybean Tissue Culture

Soybean tissue capable of regeneration to whole plants are grown in the presence of F. solani or extracts thereof. Cell lines representing mutants capable of continued growth are regenerated and the heritability of SDS determined in these plants or their seed or tissue derived progeny.

EXAMPLE 7

Marker Assisted Selection and Greenhouse Selection for Resistance to SDS

Materials and Methods

The genetic material used included 30 $F_{5:10}$ recombinant inbred lines (RILs) (a subset of a population of 100 lines) from the cross of 'Essex' (Smith and Camper, 1973)× 'Forrest' (Hartwig and Epps, 1973). Essex is susceptible to SDS while Forrest is resistant to SDS (Gibson et al., 1994; Hnetkovsky et al., 1996). The RILs were selected to include three groups (10 RILs per group) based on SDS disease data from five field environments over five years ($F_{5:6}$ to $F_{5:10}$). The groups were: (1) field SDS-resistant (10 best of the 100 lines); (2) field SDS-moderate (middle 10 of the 100 lines); and (3) field SDS-susceptible (10 worst of the 100 lines). Essex and Forrest were included for comparison.

The *F. solani* isolate (ST90) used in these assays was isolated from SDS infected roots of the soybean cultivar Spencer in Stonington, Ill. The isolation process has been described by Stephens et al., (1993). A 1:1 mixture of cornmeal and $SiO_2$ (SIGMA Chemical Co., St Louis, Mo.) was infested with *F. solani* (ST90) and allowed to incubate for 10 days after O'Donnell and Gray (1995). Five $cm^3$ of the inoculum were added to 250 ml of setrile water. The average count of spores on ten 1 ml samples, examined on a hemocytometer under a microscope indicated that the initial inoculum density was $4 \times 10^5$ spores per $cm^3$.

Three experiments were conducted in the greenhouse. The first two experiments were designed to evaluate the selected genotypes in the greenhouse for SDS disease severity (DS) using three inoculum densities (high=$10^4$, medium=$5 \times 10^3$, and low=$3.3 \times 10^3$ spore per $cm^3$ of soil). The third experiment was designed to evaluate the genotypes in the greenhouse for *F. solani* root infection severity (IS) using one inoculum density ($2 \times 10^3$ spore per $cm^3$ of soil).

Sterile soil consisting of a 1:1 (v/v) mixture of sterile sand and soil was used in all experiments. Inoculum and soil were mixed in three ratios (v/v) (1:40, 1:80, and 1:120) for the first two experiments; and in one ratio (v/v) (1:200) for the third. All experiments were planted in a randomized complete block design with two replications. Two-week-old seedlings were transplanted into the inoculated mixture in styrofoam cups and kept saturated with water for four weeks. Experiments were conducted between November 1st and March 1st. Plants were grown with a 14-hour photoperiod and the air temperatue was from 20-27° C.

The first two experiments were rated for SDS disease severity (DS) at 21 d after inoculation. The DS was rated on a scale of 1 to 9 as described by Njiti et al., (1996). The third experiment was evaluated for IS 21 d after inoculation. Roots were collected and each was washed, oven-dried at 45° C. for 48 h, ground using a Wiley cutting mill (Thomas Scientific™, Swedesboro, N.J.), weighed, and added to 2,000 ml of distilled water one ml of the suspension was transferred onto each of five petri plates containing a modified Nash and Snyder's medium consisting of 20 g agar, 15 g peptone, 1 g $KH_2PO_4$, 0.5 g $MgSO_4.7H_2O$ and 1 L distilled water (Nash and Snyder, 1962). After autoclaving for 40 min and cooling to 45° C. we added, 0.3 g streptomycin sulfate, 0.1 g neomycin, 0.1 g chlortetracycline, 0.05 g rifampicin, and 0.23 g pentachloronitrobenzene (PCNB) (Terrachlor, Uniroyal Chemical Co., Vaugntuk, Conn.). Plates were incubated at room temperature for 14 d. The number of slow-growing fungus colonies with slimy colony morphology and little aerial mycelium (Rupe, 1989) (see arrows in FIG. 1) on each plate was counted as colony forming units (CFU). The CFU per gram of root tissue was calculated and used for analysis.

Because of the wide range, CFU values were square root transformed for all variance components analyses. Data were subjected to analysis of variance (ANOVA) (SAS Institute Inc., Cary, N.C.). Genotype within group by experiment interaction was tested to justify pooling data from the two experiments. Mean comparison by LSD (Gomez and Gomez, 1984). Data were compared against markers that have been previously shown to be associated with SDS resistance in the field by a one way ANOVA (Chang et al., 1996). Correlations were determined using the CORR function of MSTATC (Freed et al., 1990).

Results

The heritability of DS in the greenhouse was 63%, 35%, and 34% for the low, medium and high inoculum densities respectively. IS heritability was 66 percent. The SDS susceptible group means for DS and IS at low inoculum density were significantly higher than those of the moderate and resistant groups (Table 14). DS and IS values from the low inoculum density treatment were significantly correlated with both field DS and disease index (DX) (Table 16). When both greenhouse DS (=<1.9) and IS (=<400) were used as selection criteria for field resistance, all the SDS field susceptible and eight of the 10 field moderate genotypes were eliminated but only four of the 10 partially field resistant genotypes were eliminated (Table 15). These results demonstrate that the combined use of DS and IS values obtained at inoculum densities of less than $3 \times 10^3$ spore per $cm^3$ of soil is an effective method of selection of soybean genotypes with high resistance to SDS. Both DS and IS from the low inoculum density assays were significantly (P=<0.05) associated with DNA markers that indentify major SDS resistance QTLs in the field (Table 17). These resu;ts show that a low inoculum greenhouse assay can be used to supplement marker assisted selection for partial field resistance to SDS.

Table 14. SDS group mean comparison of *F. solani* infection severity (IS) as colony forming units (CFU) per gram of soybean roots.

| SDS group | IS mean (CFU/g of tissue) |
|---|---|
| SDS-resistant | 400 A† |
| SDS-moderate | 598 A |
| SDS-susceptible | 1324 B |

†Means followed by the same letter are not significantly different.

Table 15. Comparison of disease severity (DS) and *F. solani* root infection severity (IS) among all genotypes at low inoculum density in the greenhouse with field DX, DS, and diagnostic DNA markers.

| SDS Grp. Genotype | Fld† K455D | GH | Fld. DX | Fld. DS | GH DS | GH IS | OI03 450 | SATT 309 | OE02 1000 |
|---|---|---|---|---|---|---|---|---|---|
| (ExF) 78 | R F | R | 0.1 | 1.1 | 1.8 | 185 | F | F | E |
| (ExF) 23 | R E | R | 0.5 | 1.1 | 1.3 | 107 | F | F | F |
| (ExF) 59 | R E | S | 0.5 | 1.2 | 1.3 | 466 | F | F | F |
| (ExF) 67 | R — | S | 1.1 | 1.2 | 2.8 | 1369 | F | F | F |
| (ExF) 57 | R — | R | 1.1 | 1.3 | 1.9 | 117 | F | F | F |
| (ExF) 44 | R F | S | 1.1 | 1.3 | 2.7 | 300 | — | E | F |
| (ExF) 20 | R E | R | 1.2 | 1.2 | 1.2 | 249 | E | F | F |
| (ExF) 47 | R E | S | 1.5 | 1.2 | 3.0 | 804 | F | F | E |
| (ExF) 37 | R E | R | 1.9 | 1.2 | 1.3 | 283 | F | F | F |
| (ExF) 55 | R E | R | 3.0 | 1.1 | 1.9 | 73 | F | F | — |
| Forrest‡ | | | 2.4 | 1.2 | 1.4 | 312 | | | |
| (ExF) 46 | M — | S | 5.4 | 1.4 | 1.5 | 615 | F | F | — |
| (ExF) 14 | M F | S | 6.3 | 1.3 | 3.4 | 501 | E | E | F |
| (ExF) 91 | M — | S | 6.4 | 1.3 | 1.3 | 601 | — | E | F |
| (ExF) 75 | M — | S | 6.4 | 1.4 | 2.0 | 202 | F | F | F |
| (ExF) 49 | M F | S | 6.9 | 1.3 | 1.8 | 505 | — | E | F |
| (ExF) 26 | M E | R | 7.2 | 1.4 | 1.4 | 369 | F | F | E |
| (ExF) 6 | M E | R | 8.2 | 1.5 | 1.2 | 199 | F | F | E |
| (ExF) 73 | M F | S | 8.6 | 1.5 | 2.2 | 312 | F | F | F |
| (ExF) 97 | M F | S | 9.1 | 1.4 | 2.5 | 1137 | E | — | E |
| (ExF) 45 | M F | S | 9.7 | 1.4 | 1.9 | 1291 | E | E | F |
| Essex‡ | | | 12.8 | 1.7 | 2.7 | 1195 | | | |
| (ExF) 7 | S E | S | 20.3 | 2.2 | 3.2 | 67 | E | E | E |
| (ExF) 80 | S F | S | 20.2 | 2.1 | 3.6 | 4407 | E | E | — |
| (ExF) 85 | S F | S | 19.8 | 2.3 | 4.9 | 1155 | E | E | E |
| (ExF) 76 | S — | S | 18.7 | 2.3 | 3.0 | 1117 | E | E | E |
| (ExF) 83 | S F | S | 18.7 | 1.9 | 3.5 | 2854 | E | E | — |
| (ExF) 18 | S F | S | 18.6 | 2.1 | 4.1 | 242 | E | E | — |
| (ExF) 68 | S F | S | 18.2 | 2.1 | 1.9 | 2037 | E | E | — |
| (ExF) 10 | S F | S | 17.5 | 2.0 | 4.4 | 574 | F | E | E |
| (ExF) 51 | S F | S | 16.0 | 2.0 | 2.5 | 244 | F | E | E |
| (ExF) 39 | S E | S | 15.7 | 2.3 | 3.2 | 549 | E | E | E |

†SDS resistance group (R = SDS-resistant, M = SDS-moderate, and S = SDS-susceptible based on field response.
‡Forrest is resistant and Essex is susceptible to SDS.

TABLE 16

| Greenhouse | Field DS | Field DX | Greenhouse† DS | IS |
|---|---|---|---|---|
| Field DS | — | 0.95*** | 0.70*** | 0.39* |
| Field DX |  | — | 0.68*** | 0.48** |
| Greenhouse DS |  |  | — | 0.37* |
| Greenhouse IS |  |  |  | — |

*, , *, significant at 5%, 1% and 0.1% probability levels respectively.
†Only the greenhouse DS values from the low inoculum density treatment was used in this table. Correlations values from the other treatments are discussed in the text.

Table 17. Associations between DS and IS from low inoculum density in the greenhouse and DNA markers that identify SDS resistance QTLs in the field.

TABLE 17

|  | $R^2$ | Prob. | Allelic Means Essex | Allelic Means Forrest |
|---|---|---|---|---|
| OI03$_{450}$ |  |  |  |  |
| Greenhouse DS | 24 | 0.0091 | 3.1 ± 0.3 | 2.1 ± 0.2 |
| G-house IS | 20 | 0.0181 | 1315 ± 398 | 441 ± 94 |
| Field DS | 40 | 0.0004 | 1.9 ± 0.1 | 1.4 ± 0.1 |
| Field DX | 42 | 0.0003 | 15.2 ± 2.0 | 5.5 ± 1.3 |
| SATT309 |  |  |  |  |
| Greenhouse DS | 38 | 0.0004 | 3.1 ± 0.3 | 1.8 ± 0.2 |
| Greenhouse IS | 18 | 0.0210 | 1096 ± 304 | 382 ± 95 |
| Field DS | 49 | 0.0001 | 1.9 ± 0.1 | 1.3 ± 0.03 |
| Field DX | 56 | 0.0001 | 14.3 ± 1.6 | 3.3 ± 0.8 |
| OE02$_{1000}$ |  |  |  |  |
| Greenhouse DS | 17 | 0.0531 | 2.7 ± 0.3 | 1.9 ± 0.2 |
| Greenhouse IS | 00 | 0.8170 | 524 ± 121 | 485 ± 112 |
| Field DS | 36 | 0.0026 | 1.7 ± 0.1 | 1.3 ± 0.0 |
| Field DX | 34 | 0.0035 | 11.4 ± 2.2 | 4.0 ± 0.9 |
| K455D |  |  |  |  |
| Greenhouse DS | 23 | 0.0229 | 1.9 ± 0.3 | 3.0 ± 0.3 |
| Greenhouse IS | 16 | 0.0527 | 316 ± 74 | 1124 ± 331 |
| Field DS | 09 | 0.1502 | 1.4 ± 0.1 | 1.7 ± 0.1 |
| Field DX | 17 | 0.0439 | 6.0 ± 2.2 | 12.2 ± 1.9 |

EXAMPLE 8

Marker Assisted Selection for SDS Resistance in the Field

Materials and Methods
Genetic Material

| Year One | Cross between soybean cultivars Flyer, susceptible to SDS and SCN & Hartwig, resistant to both. |
|---|---|
| Year Two | $F_2$ seeds generated were used to produce $F_3$ seeds by single pod decent. |
| Year Three | Advanced to $F_5$ in the winter nursery in Puerto Rico |
| Year Four | 786 individual $F_5$ plants were randomly harvested as RILs. |
| Year Six | 400 lines grown at ARC to select lines--94 sent to Puerto Rico for increased seed supply |
| Year Seven | $F_{5:6}$ seed were planted in greenhouse and leaf samples were used for analysis on all 786 and $F_{5:8}$ seeds on 50 recombinant inbred lines planted in field for SDS rating. |

Marker Methodology

Approximately 100 ng (enough for 20 reactions) of PCR ready DNA was extracted from 50 mg of fresh young leaf tissue using a Matrix Mill. The Matrix Mill uses a 30 second burst of an electromagnetically driven metal pestle. BLT65 was amplified using SCAR primers and was visualized on 1.4% agarose gel. SATT38 was amplified using microsatellite primers and was visualized on high resolution FMC agasrose gel. BLT65 was scored as S=single band and R=double band. SATT38 was scored as S, with about 10% more bp., as being slightly higher than R.

Two Markers Used to Identify Four Groups

| pBLT65 Maps close to SCN resistant gene Rhg4 SATT38 Maps close to the SDS resistant rfs1, rft1 and SCN resistant gene rhg1 | | | | |
|---|---|---|---|---|
|  | Marker 1 | Marker 2 | Class | N |
| Group 1 | pBLT65 (H) | SATT38 (H) | R/R | 12 |
| Group 2 | pBLT65 (H) | SATT38 (F) | R/S | 11 |
| Group 3 | pBLT65 (F) | SATT38 (H) | S/R | 9 |
| Group 4 | pBLT65 (F) | SATT38 (F) | S/S | 18 |

Field Test

Two locations, Ridgway and Ullin, were selected for this study based on a history of uniform SDS symptoms. Genotypes were planted in a randomized complete block design in 2 row plots in 2 replications. Data was collected twice from each location at R6—only 3 plants due to yield concerns and R8—five plants. Roots were transported in a cooler to the laboratory where they were stored at 4° C. (1-7 days) until they were processed for *F. solani* isolation and quantification.

Restrictive Medium

A restrictive medium was prepared as follows:
960 mL of distilled water
0.012 g/mL potatodextrose agar (PDA)
0.012 g/mL agar
10 mL/L of 10% (v/v) tergitol NP-10
Autoclaved and cooled to about 60 C
Fungistatic Antibiotics—limited fungal growth
10 mL/L of 0.025 g/mL penta-chloro-nitro-benzene [PCNB, 75% (w/v)]
10 mL/L of 0.002 g/mL of 2,6-dichloro-4-nitroaniline sold under the registered trademark BOTRAN®
Bacteriocidal Antibiotics—restricted bacterial growth
10 mL/L of 0.012 g/mL of tetracycline
10 mL/L of 0.012 g/mL of neomyucin sulfate
10 mL/L of 0.012 g/mL of streptomyucin
10 mL/L of 0.012 g/mL of rifampicin (2nd sampling only)

Thus, by the term "restrictive medium" it is meant a growth medium that allows for limited fungal growth or slow fungal growth, while at the same time substantially restricting and/or preventing bacterial growth.

Root Preparation

Roots were cut and lateral roots were removed. The lateral roots were then washed to remove all soil & rinsed in distilled water. The root surface was sterilized in 100 mL/L NaClO for 3 minutes. The roots were then dipped in dulute (40 μg/mL) tetracycline solution (sterile conditions). Ten 1" segments were randomly selected and placed on the restrictive medium. Each plant was treated separately, then incubated at room temperature for 14 days.

Quantification

*F. solani* is slow growing and stains PDA medium blue. For each plate, we counted the number of slow-growing blue fungi. This number was expressed as a percentage of the total number of pieces. The percentage of segments yeilding blue *F. solani* from all sampled plants of each plot were determined as infection severity (IS). The data were subjected to ANOVA, with the mean separation by LSD.

Results

At Ullin, higher infection severity maybe due to wet conditions immediately after planting. At Ridgway, low infection severity maybe due to late planting and dry conditions immediately after planting. Leaf scorch was not measurable (DX<1) at either location, possibly due to a combination of late planting and dry conditions during the reproductive period. The increased sensitivity of IS evaluation by addition of rifampicin in selective medium increased the number of *Fusarium solani* colony forming units on second sampling.

We found SATT38 to be effective in selecting soybean cultivars with resistance to infection by *F. solani*. The use of pBLT65 in addition to SATT38 for MAS did not improve resistance to infection compared to the use of SATT38 alone. Both SATT38 and pBLT65 were required for SCN resistance to be present indicating digenetic inheritance.

In summary, allelles or genes conferring partial resistance to SDS in E×F function to confer resistance across crosses, across resistant cultivars, across genetic backgrounds, across growth habits, and across maturity groups. Allelles or genes conferring resistance to SCN in E×F function to confer resistance across crosses, across resistant cultivars, across genetic backgrounds, across growth habits, and acrross maturity groups.

TABLE 18

ANOVA for markers selection

| Source | df | ULLIN MS | ULLIN P > F | RIDGWAY MS | RIDGWAY P > F |
|---|---|---|---|---|---|
| Sample 1 | | | | | |
| Rep | 1 | 2057 | 0.0100 | 109 | 0.3892 |
| Grp | 3 | 232 | 0.4921 | 237 | 0.1925 |
| Gen (Grp) | 46 | 422 | 0.0927 | 151 | 0.4353 |
| SDS-R v SDS-S | 1 | 440 | 0.2201 | 109 | 0.3890 |
| Grp x Rep | 3 | 438 | 0.2171 | 354 | 0.0750 |
| Error | 46 | 285 | | 144 | |
| Sample 2 | | | | | |
| Rep | 1 | 486 | 0.1899 | 208 | 0.3619 |
| Grp | 3 | 2874 | 0.0001 | 508 | 0.1178 |
| Gen (Grp) | 46 | 380 | 0.0836 | 324 | 0.1764 |
| SDS-R v SDS-S | 1 | 8021 | 0.0001 | 1430 | 0.0199 |
| Grp x Rep | 3 | 277 | 0.3544 | 246 | 0.9920 |
| Error | 46 | 249 | | 8 | |

TABLE 19

Marker assisted selection for SDS and SCN in Hartwig by Flyer derived recombinant inbred lines. Numbers in columns followed by letters that differ indicate means that are significantly different.

| | Marker 1 | Marker 2 | Class | N | % Infection Severity Ullin | % Infection Severity Ridgway | % Infection Severity Mean | SCN score |
|---|---|---|---|---|---|---|---|---|
| Group 1 | pBLT65 (H) | SATT38 (H) | R/R | 12 | 34a | 25a | 29a | 2.03a |
| Group 2 | pBLT65 (H) | SATT38 (F) | R/S | 11 | 47b | 24a | 35b | 3.74b |
| Group 3 | pBLT65 (F) | SATT38 (H) | S/R | 9 | 35a | 21a | 28a | 3.16b |
| Group 4 | pBLT65 (F) | SATT38 (F) | S/S | 18 | 48b | 27a | 37b | 2.99b |

References

U.S. Patent Documents

U.S. Pat. No. 5,612,191 March 1997 Briggs et al.
U.S. Pat. No. 5,606,823 March 1997 Souza et al.
U.S. Pat. No. 5,574,210 November 1996 Saghai-Maroof et al.
U.S. Pat. No. 5,536,901 July 1996 Greaves et al.
U.S. Pat. No. 5,492,547 February 1996 Johnson
U.S. Pat. No. 5,491,081 February 1996 Webb
U.S. Pat. No. 5,476,524 December 1995 Leon et al.
U.S. Pat. No. 5,385,835 January 1995 Helentjaris et al.

Other Publications

Abu-Thredeih et al. (1996) *Soybean Genetics Newsletter* 23:158-162.
Achenbach et al. (1996) *Plant Dis.* 80:1228-1232.
Akkaya et al. (1995) *Crop Sci.* 35:1439-1445.
Chang et al. (1996) *Crop Sci.* 36:1424-1428.
Chang et al. (1997) *Crop Sci.* 37(3):965-971.
Concibido, V. (1996) *Theor Appl. Genet.* 93:234-241.
Gibson et al. (1994) D. Wilkinson (ed.) *Proc. Twenty-fourth Soybean Seed Res. Conf.*, Chicago, Ill. 6-7 December, Am. Seed Trade Assoc., Washington D.C. (pp. 20-40).
Gribskov et al. (1986) *Nucl. Acids Res.* 14:6745.
Hartmann et al. (1995) *Plant Disease* 79:314-318.
Hartwig et al. (1973) *Crop Sci.* 13:287.
Hnetkovsky et al. (1996) *Crop Sci.* 36(2):393-400.
Fehr, R. W. (1987) *Breeding Methods for Cultivar Development*, in J. R. Wilcox (ed.) *Soybeans: Improvement Production and Uses*, 2d. ed.
Kanehisa (1984) *Nucl. Acid Res.* 12:203-213
Keim et al. (1989) *Theor. Appl. Genet.* 77:786-792.
Kilo et al. (1996) *Agronomy Abstracts*, pp. 94.
Landers et al. (1989) *Genetics* 121:185-199.
Matthews et al. (1991) *Soybean Genetics Newsletter.*
Mulrooney, R. P. (1988) *Plant Dis.* 72:915.
Myers et al. (1988) *Crop Sci.* 28:375-376.
Needleman et al. *J. Mol. Biol.* 48:443.
Njiti et al. (1996) *Crop Sci.* 36:1165-1170.
Njiti et al. (1997) *Crop Science* 37:132-138.
O'Donnell et al. (1995) *Molec. Plant Micr. Inter.* 8:709-716.
Roy et al. (1989) *Phytopathology* 79:191-197.
Rupe et al. (1991) *Plant Dis.* 75:47-50.
Rupe, J. C. (1989) *Plant Dis.* 73:581-584.
Sambrook, et al. *Molecular Cloning Laboratory Manual*, 2d Edition, 1989.

Schwartz et al., eds., *Atlas of Protein Sequence and Structure*, National Biomedical Research Foundation, pp. 353-358, 1979.
Shoemaker et al. (1995) *Crop Sci.* 35:436-446.
Smith et al. (1973) *Crop Sci.* 13:459.
Smith et al. (1981) *Adv. Appl. Math.* 2:482.
Stevens et al. (1993c) *Crop Sci.* 33:929-930.
Torto et al. (1996) *Soybean Genetics Newsletter* 23:163-166.
Vos et al. (1995) *Nucleic Acids Research* 23:4407-4414.
Webb et al. (1994) *Theor. Appl. Genet. (in press).*

Wetmur & Davidson (1968) *J. Mol. Biol.* 31:349-370
Williams et al. (1990) *Nucl. Acids Res.* 18:6531-6535.
Wrather et al. (1996) *Plant Disease* 80:
Wrather et al. (1995) *Plant Disease* 79:1076-1079.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of characterizing resistance to soybean sudden death syndrome in a soybean plant, the method comprising the steps of:

(a) isolating root pieces from a soybean plant infected by *Fusarium solani,*

(b) culturing the root pieces on a culture plate including a restrictive growth medium that provides for slow fungal growth and restricted bacterial growth;

(c) determining root infection severity by statistically evaluating the number of *Fusarium solani* colony forming units on said culture plate, wherein the statistically evaluating comprises counting the number of CFU, and expressing the number of CFU as a percentage of a total number of root pieces; and (d) characterizing resistance to soybean sudden death syndrome in said soybean plant based on said determined root infection severity.

2. The method of claim 1, wherein said characterization of resistance to soybean sudden death syndrome further comprises determining a level of resistance to soybean sudden death in the soybean plant based on a disease severity value, an infection severity value or both a disease selection value and an infection severity value.

3. The method of claim 1, wherein the restrictive growth medium comprises one or more fungicidal antibiotics and one or more bacteriocidal or bacteriostatic antibiotics.

4. The method of claim 3, wherein the one or more fungicidal antibiotics are selected from the group consisting of 2,6-dichloro-4-nitroaniline and pentachloronitrobenzene and the one or more bacteriocidal or bacteriostatic antibiotics are selected from the group consisting of tetracycline, neomycin, streptomycin, and rifampicin.

5. The method of claim 4, wherein at least one of the one or more bacteriocidal or bacteriostatic antibiotics is rifampicin.

* * * * *

SEQUENCE LISTING

<160> NUMBER OF SEQ ID NOS: 20

<210> SEQ ID NO 1
<211> LENGTH: 527
<212> TYPE: DNA
<213> ORGANISM: Glycine max
<220> FEATURE:
<221> NAME/KEY: misc_feature
<222> LOCATION: (1)..(527)
<223> OTHER INFORMATION: n is a, c, g, or t/u

<400> SEQUENCE: 1

```
tgttctagat agttcgcaat tcaatcaaat ttcccaatta taattgaata aaaagattca      60
tgaaatcagg tgatcaagcg aaaataagc attaagcgta gaagagaagc aataacattt     120
ttttattaaa taataaaaga gtaattacat aaaaatatgt tcgattacat taaaccccaa    180
caaaggatga atttagcttc tcatgaccat ggggaaaatc aaacttgatg aacaagaaga    240
tgaagaagaa tccttaagga taaacactgc ctagctccaa tgtgctctct agtattttat    300
ctttcaaaaa tccccaagaa cccctaattt tcagtaagaa gcccattttc aatcagaagc    360
ccattttcaa tcaagaagcc cattttcaat cagaagccca ttttcaatca gaagcccatt    420
ttcaatcaga agcccatttt caatcagaag cccattttat aattgtattc ccaaaacttg    480
agattcttga acgtaaatta ttagtaaatt gtaatcacct ctgtaaa                   527
```

<210> SEQ ID NO 2
<211> LENGTH: 815
<212> TYPE: DNA
<213> ORGANISM: Glycine max
<220> FEATURE:
<221> NAME/KEY: misc_feature
<222> LOCATION: (1)..(815)
<223> OTHER INFORMATION: n is a, c, g, or t/u

<400> SEQUENCE: 2

```
atgattacgc caagctattt aggtgacact actagaatac tcaagctatg catccaacgc      60
gttgggagct ctcccatatg gtcgacctgc aggcggccgc actagtgatt cagaagccca    120 aagtaacag caataagtaa tcccttgttt ataagatccc agaacttcca gtttatttaa    180
tgaaaatgca ataacatcgg ctagtttcac aagtaatata caaatcggaa catcacattg    240
actacaatat atagtacata aattaacact aagaaacctc cttgatttga tattatgcat    300
ttacctatgt tgttccacaa gaatatactc aaatgacttt gccttgattt aaattatcac    360
gatgtaacac aaacaaagat gatantttgt cgatcaactg ttcagcacca agagagccct    420
ccccacaatc aactcaggtt ttcacttttg gtgcttgaaa atgagtggca catgnaaaag    480
caagagtcnt ctttgacaaa tgtgcctgcc ganagttatc antacttact aacaagataa    540
tgagccaaaa catcatctgg gncatcaacc ttcatgnctt tntcaagttt atacctatna    600
```

| | |
|---|---|
| ntnactangt cttatatttn canntggtga ttacanttac nantaagttt agcttnaaga | 660 |
| aatncaagtt ttngggactc catgcctngn cnggntttcn natccgtcgg ccagggcggn | 720 |
| cnggnncact gntnggnagn cccanttncn cagancacng nccntttcc attccnggnc | 780 |
| cntcnncttc aangacngcc ggngaaancn ngggt | 815 |

<210> SEQ ID NO 3
<211> LENGTH: 435
<212> TYPE: DNA
<213> ORGANISM: Glycine max
<220> FEATURE:
<221> NAME/KEY: misc_feature
<222> LOCATION: (1)..(435)
<223> OTHER INFORMATION: n is a, c, g, or t/u

<400> SEQUENCE: 3

| | |
|---|---|
| gcagatgtaa ctgttcccac aatatctaat attctagttc tagatgaaaa tatttttttc | 60 |
| ccatagcaag caaagtatgg atttgtcatt tttcagagac gaagaactct caacaaacat | 120 |
| gtttatagta acttcattgc aaaactcaac aaatagattt ttggaacctt aatataataa | 180 |
| aattcaacag tcttctttaa ttttattctg ctcttacctt tcataggat catatagaat | 240 |
| ttaaccctac aagctctcaa aaacaatcc attattatgc tccttatcca ataaaacaaa | 300 |
| accatagagt gattctcaaa atgaagattg acaaaggcaa aaagttatgc tggntcaata | 360 |
| gcttctttat aattntcttc atcttgcacc ntcccngcct taggnggtct ccattgtcaa | 420 |
| tccaaaggtn ntcgn | 435 |

<210> SEQ ID NO 4
<211> LENGTH: 183
<212> TYPE: DNA
<213> ORGANISM: Glycine max
<220> FEATURE:
<221> NAME/KEY: misc_feature
<222> LOCATION: (1)..(183)
<223> OTHER INFORMATION: n is a, c, g, or t/u

<400> SEQUENCE: 4

| | |
|---|---|
| ggtacccggg gatcctctag agtcgacctg cagggaggcg aatgtnatgt tganctttgc | 60 |
| tcgctcatat ggccttacag ggtttgccga attagtgtga aggtaattcg gtaaatggat | 120 |
| aatattgtat tcatttnata tttnatgatg ttacaagtnc aaggnataan ctgatgcctg | 180 |
| agt | 183 |

<210> SEQ ID NO 5
<211> LENGTH: 499
<212> TYPE: DNA
<213> ORGANISM: Glycine max
<220> FEATURE:
<221> NAME/KEY: misc_feature
<222> LOCATION: (1)..(499)
<223> OTHER INFORMATION: n is a, c, g, or t/u

<400> SEQUENCE: 5

| | |
|---|---|
| caggtagaca aatctgatgg tactgaagtt ggtcatacaa ttaaaaagtt ccctctttta | 60 |
| aagcccagag aatatgtgct agcttggaag tngtgggagg ggagtgatga acatttttac | 120 |
| tgttttatga aggtaataca ccaattatta tggttttttg tttaataaaa tgtgaataat | 180 |
| tgtcaatcgt gattgcatta tctctccttt actctgtctc ttcaccttt ttacccttt | 240 |
| atttgagagg aagaatccat gtagtaaaaa atgatgataa aattgttaga aaatatagtg | 300 |

```
tcatgtaatt agagattcag attataactt agaagacact attattttca tgtaatacta      360
tccacgggta attatcaata ctgacatatt ttcactcaaa atattctggt tttctcatta      420
tatacattta aataggagct attanccatt gcaagcttgg gtttggaggc cttccgatgc      480
cttgttggga ttgngacca                                                  499
```

<210> SEQ ID NO 6
<211> LENGTH: 500
<212> TYPE: DNA
<213> ORGANISM: Glycine max
<220> FEATURE:
<221> NAME/KEY: misc_feature
<222> LOCATION: (1)..(500)
<223> OTHER INFORMATION: n is a, c, g, or t/u

<400> SEQUENCE: 6

```
nagncaggga acccacacat acagacaatt aaaaccgttg gatgaaaatc atactactca       60
taaattgaaa atatatacgt aagancttca tctaacagtg ctagtcgaag aatgcgtaaa      120
tgcaggnnat ccatttccat actaaaatgg acaaaactta tattttttttt ttagcggcaa    180 acgttaatta ttaattttttt ttagtacaag ggatcaaacc angacctttc ccttctttcc    240
atctttcttg accacccaac caaccttata tctccacaaa acttattata tgttgttctt    300
cggggactat cagaattgga gtttaacctc gggcantcaa tctacataat ccttgatttn    360
atttngtgaa gttctaaagc cacaggcatt atttatntta ttntttctgn agtaacccnc    420
catatgttgg tnnataaggg tangnataaa aatncnttgg ntggtnncna tttgcncttn    480
cnaggccggg gatggntttt                                                500
```

<210> SEQ ID NO 7
<211> LENGTH: 189
<212> TYPE: DNA
<213> ORGANISM: Glycine max
<220> FEATURE:
<221> NAME/KEY: misc_feature
<222> LOCATION: (1)..(189)
<223> OTHER INFORMATION: n is a, c, g, or t/u

<400> SEQUENCE: 7

```
nnacaanana ncaggggatc ctctagagtc gacctgcagt gatactagaa ctnaatgaac       60
agggagagag agagagagag aganantnaa nataacgatg aagctctccc tattgacggt     120
gttcattgta gcaatagcat cgttatctct tattattgct ggttcatcat natctcaatt    180
ccagtggca                                                             189
```

<210> SEQ ID NO 8
<211> LENGTH: 724
<212> TYPE: DNA
<213> ORGANISM: Glycine max
<220> FEATURE:
<221> NAME/KEY: misc_feature
<222> LOCATION: (1)..(724)
<223> OTHER INFORMATION: n is a, c, g, or t

<400> SEQUENCE: 8

```
aatttttttat ataagttgca aaatttaggg acttatttat tattaaatta tttgtaggga      60
ctaatttatc atattttttg tatattcagg aattaaattt aatttttcat ccttcaatac     120
taacttatta acgtttcaca ttttcaaaga cgagtctagc tatttataat ttttttttcct   180 aaaatatatt ttttgtcctc ataaaatgaa aaatatttaa aattcgttcc taattttttt    240
ttcaaagcat ctttccttct cacaaaattg aaatgtatca ttttttttttg ttcaaaagtt   300
```

-continued

```
taaataaatt tgaacctaat atgcatttt atatcggtta tacatataac tgatataaac      360
atcaagtttt ttatatcaat gatacctata actgatatca aatgtgacaa ttatatatat      420
aattaatgta aaaagtcat aaatataatt tattttgagt caaaaaataa tatattttaa      480
ttattttgaa gatgaaaaag gataaattta aaacatttgt gtgangatga aaaactagat     540 gtttttttc ctggtttaaa tgcaaaacca atgctattt atttaaattt tacctttttt       600
ttataattac nccaccaaaa aaccgtttgg tgttacaaat ttganttaaa ttctnttgtt     660
tattaaaaag ananattaat tnggaanggt cttttnaaa acnctncngt cnantaacna      720
atct                                                                  724
```

<210> SEQ ID NO 9
<211> LENGTH: 801
<212> TYPE: DNA
<213> ORGANISM: Glycine max
<220> FEATURE:
<221> NAME/KEY: misc_feature
<222> LOCATION: (1)..(801)
<223> OTHER INFORMATION: n is a, c, g, or t

<400> SEQUENCE: 9

```
acgccagtga ntgtaatacg actcctatag ggcgaattgg ccaagtcggc cgagctcgaa      60
ttcgtcgacc tcgagggatc acgctaatga tatattatta atcaactgct tcaatagagt     120
gcacacaccc tatctttcat aaaattacta cactttttaa tttttgtaat aaaaaaccta     180
gaaaaactca ttatgaaaca gatgatgtac ttttaacact ctgtcggcct ctctctctct     240
attatatatt gatttaaatt tattgagaat tatattttg ttgggtctca tttattatat     300
tttattaatt ggatccgggc cctctagatg cggccgcatg cataagcttg agtattctat     360
agtgtcacct aaatagcttg gcgtaatcat ggtcatagct gtttcctgtg tgaaattgtt     420
atccgctcac aattccacac aacatacgag ccggaagcat aaagtgtnaa gcctggggtn     480
cctaatgagt gagctaactc acattaattg ccttgcgctc actgcccgct ttccagtcng     540
gaaacctgtc ctgccagctg cattaatgaa tcngccaacc cncggggana agcngtttgc     600
ntatgggcgc tcttnccgct tcctcgctca ntgactcgct gcgctcngtc nttcngntgc     660
cgcgaacggt atcancncac tcnaangnng taaatacgt tatccaccna accnggggga      720
naacccngga aaaacatgt nanccaaaag gccnccaaaa ggccangaaa cnttnaaaag     780
gcccnnttgc ttgncttnt n                                                801
```

<210> SEQ ID NO 10
<211> LENGTH: 809
<212> TYPE: DNA
<213> ORGANISM: Glycine max
<220> FEATURE:
<221> NAME/KEY: misc_feature
<222> LOCATION: (1)..(809)
<223> OTHER INFORMATION: n is a, c, g, or t

<400> SEQUENCE: 10

```
nnnnnnttgt aaacgacgca gtgaatgtat acgaccacta tagggcaatg gccaagtcgg      60
ccgagctcga attcgtcgac ctcgagggat cttttatgt tggtagctac tgtaatatca     120
tcttgtactt ttaacttta agtcatactc ccttggact catatataag caaaagagtg      180
gtcttgtatg tcggacttaa atataagcaa atctaactaa ttttgtccta tttaatactt     240
tcattcctaa aacacccttc atttaattct aattctattt ccaataactc ttttttattc     300
```

-continued

| | |
|---|---|
| atgataacaa gttccaatga aggacatttt agaaataacc ttatttttta tttgagatta | 360 |
| gtaaaattaa atgatgtgaa ctaactttct taattaatgt gaaattagtt attttttctt | 420 |
| atatacgagt ccaaagggag taccaaattt cacaaatgta ctaaaatgta ttatatgctt | 480 |
| cttttttaatt catctttgct gcatanctac ttagctactg tgctctgatc cgggccctct | 540 |
| agatgcggcc gcatgcataa gcttgagtat ctatagtgtc cctaaatagc ttggcgtatc | 600 |
| atggtcatag ctgtttccng tgtgaaattg ttatccgctc acaattccac acaacatacg | 660 |
| anccggaagc ataaaagtgt taagccnggg gtgcctaatg agtgagctaa ctcacattaa | 720 |
| ttgcgttgcg ctcactgccc gcttccnatt cgggaaactg tcctgncanc tgcattaatg | 780 |
| aatcnggcca acccncnggg aaaaggcgg | 809 |

<210> SEQ ID NO 11
<211> LENGTH: 810
<212> TYPE: DNA
<213> ORGANISM: Glycine max
<220> FEATURE:
<221> NAME/KEY: misc_feature
<222> LOCATION: (1)..(810)
<223> OTHER INFORMATION: n is a, c, g, or t/u

<400> SEQUENCE: 11

| | |
|---|---|
| acngccagtg aattgtaata cgactcctat agggcgaatt ggccaagtcg gccgagctcg | 60 |
| aattcgtcga cctcgaggga tctataatat ttctgacagc tacctttta tttagcttgc | 120 |
| agagggctg attttggaga aaacatcatc catggtataa agtccgttta gattccagct | 180 |
| attgttcaca ttcatccctt acatatgaga atatccctat aagctgaaac taacttttac | 240 |
| aaacaaacat gcaccgaacc attaaagttt gacttaatat ccggggtata atgaccttaa | 300 |
| ttcagaaatt cacataaata actaaaagta agttgtattt tatttatgtc tggatttact | 360 |
| gcacaaacta aacaaaagtt tgtggattta gacataaaaa ataccaatgc tgtgtgaaaa | 420 |
| taagaaatgg tggtcatata gacaagtttc ttttctgttt tctttaaatt gcagtcnaag | 480 |
| ccatcangag gttcatgtaa ttaaccaaac tagacgttga cttttggttt tatccttttg | 540 |
| tagaatagca agcaagtcat tataaatctg gccattggga cagcttagtt taactcccgc | 600 |
| cgcaaatttg ttaaaatatt naataataat atcacctaaa atcatatttg tcanttcatt | 660 |
| ttgttttang ttatatcaat tattatttt taccttacnt cctttataat ntcaatgatg | 720 |
| ggacccaaaa aattatcaaa tacnttnaag cnttatttat tattaattaa ncctttaatt | 780 |
| ataattaaaa attcnattta attttttaan | 810 |

<210> SEQ ID NO 12
<211> LENGTH: 777
<212> TYPE: DNA
<213> ORGANISM: Glycine max
<220> FEATURE:
<221> NAME/KEY: misc_feature
<222> LOCATION: (1)..(777)
<223> OTHER INFORMATION: n is a, c, g, or t/u

<400> SEQUENCE: 12

| | |
|---|---|
| anangattcg ncagctattt aggtgacata tagaaatact caagcttatg catgcggccg | 60 |
| catctagagg gcccggatct ttcggttgaa gcaaaattga agtctttgc tcatttttat | 120 |
| caaattcttt aatgaaaagt taattacata aatatttta gtagaagcaa ttttacacag | 180 |
| ttattattta aaaaaattac acagttattc aataacaaat tacaatatat tataaggtta | 240 |
| taataaatat tttaaaattc atataaaaga tgacttatta ataagttgat aatgtaaatt | 300 |

-continued

```
ttttacacta ttaaactcat tttacgtaat cttagcgaca acatactatt tttttcatga      360
aatttacaaa aagctttcaa aaataaaatt attagttgta cccccaaaat ataaaattat      420
tagctatgtt aaaaatttgt gaatttcata aagaaaaaa atattacagt attatatatt       480
aaaattaaat ctcacaataa aaacacgtaa agttatcgtt ttgaattatt agttaaagtc      540
cttcgtctcg tattttttctc aactctaccg acagcataaa caggttgtct ccttcntaat    600
aacaatcgtg gctgggaaca aaaatcgttt ttttagaaga atcngaaatc gtattgacgg     660
tgcgttttaa aaagactatc caataatctt cttttaataa cnctgaattt cnccaattct     720
tncncaacgg ttttttggtg cgttnttta aaaaagttn aatttaatta aaatncn         777
```

<210> SEQ ID NO 13
<211> LENGTH: 775
<212> TYPE: DNA
<213> ORGANISM: Glycine max
<220> FEATURE:
<221> NAME/KEY: misc_feature
<222> LOCATION: (1)..(775)
<223> OTHER INFORMATION: n is a, c, g, or t/u

<400> SEQUENCE: 13

```
atncccnagc tattaggtga cactatagaa tactcaagct tatgcatgcg gccgcatcta     60
gagggcccgg atccaattaa taaatataaa taaatgagac caacnaaaat atattctcna    120
taaatttnaa tccatatttt antaaaaaaa aaaaggccna caaatnttta aaattcctnc    180
nncnntttca tantnatttt tcctaggttt tttattncaa aanttaaaaa ttntattant    240
tttatnaaaa atagggtntn tgcacnctat tgaaccantn nattaataat atatctttan   300
cntnatccct caaggtcaac aaanttcana ncncggccna cttggccaat tcncctata    360 gtgantcntn ttacaactca ctggccgtcg ttttacaacc tcgtgactgg gaaancctg    420 gcgttcccca anttaatcnc cttgcaacat ntcccctttc gccngctggt gttnataccn    480
aaaaggcccg cnccgatcgc ccttcccnac ttttgcgccc cctnatggc naatggacgc    540 ccctgttncg ngcncattan ncgcggcggg tgtggtggtt accccacnt gaccctacac    600 ttgccagccc cctaaccccn ccccttttcgc tttctcccct ccttttctcg ccncttcgcc    660
ggnttcccnt caagcnctaa atcggggctc ccttttagggt tccnaattaa ttgctttacg    720
gccctccacc ccaaaaactt gataagggtg atggtcncnt tctgggcnn cccn           775
```

<210> SEQ ID NO 14
<211> LENGTH: 796
<212> TYPE: DNA
<213> ORGANISM: Glycine max
<220> FEATURE:
<221> NAME/KEY: misc_feature
<222> LOCATION: (1)..(796)
<223> OTHER INFORMATION: n is a, c, g, or t/u

<400> SEQUENCE: 14

```
acntgattca ccaagctatn taggtgacta tagaatactc aagcttatgc atgcggccgc     60
atctagaggg cccggatcag agcacagtag ctaagtagct atgcagcaaa gatgaattaa    120
aaagaagcat ataatacatt ttagtacatt tgtgaaattt ggtactccct ttggactcgt    180
atataagaaa aaataactaa tttcacatta attaagaaag ttagttcaca tcatttaatt    240
ttactaatct caaataaaaa ataaggttat ttctaaaatg tccttcattg gaacttgtta    300
tcatgaataa aaaagagtta ttggaaatag aattagaatt aaatgaaggg tgttttagga    360
```

-continued

```
atgaaagtat taaataggac aaaattagtt agatttgctt atatttaagt ccgacataca    420
agaccactct tttgcttata tatgagtcca aagggagtat gacttaaaag ttnaaagtnc    480
aagatgatat tacagtagct accaacataa aaagatccct cgaggtcgac gaattcgagc    540
tcggccgact tggccaattc ccctatagtg agtcgtatta caattcactg gccgtcgttt    600
tacaacgtcn tgactgggaa aacctggcgt tccccactta tcgccttgca gcacatcccc    660
tttcgccngc tggcgtnnta ccaaaaaggc cgcaccgatc gcccttcccn acagttgccc    720 canccgtgaat ggcgaaatgg accccctgt taccggccca tttaaacccc gnngggtgtt    780 gtggttncc cncccn    796
```

<210> SEQ ID NO 15  
<211> LENGTH: 782  
<212> TYPE: DNA  
<213> ORGANISM: Glycine max  
<220> FEATURE:  
<221> NAME/KEY: misc_feature  
<222> LOCATION: (1)..(782)  
<223> OTHER INFORMATION: n is a, c, g, or t/u

<400> SEQUENCE: 15

```
attacgccaa gctattaggt gacactatag aaatactcaa gcttatgcat gcggccgcat     60
ctagagggcc cggatctttt attaaaaatt taattgagtc tcttaattat tgaaaagttt    120
aattaaatca tcaattatta aaaaaaatca accatatcct ttattgttta aacattata    180 attatgctct ttcaaccaac tctgttagtt taattgatag aagttttgta aatagatatt    240
tttacataat ataaataatc ttttttacata tattgcagcc aatgtaaaat attatctttt    300
tacattcatt gcttttgatg taaaaaatta ttgtttttaca tatgttgtat tgacaataaa    360
tataaaaata tttattttg tcaattagat taatgaactg atgatgaaaa agatataatt    420
ataatatttt taataattag agaatttgat tgaacttttt aataattaaa aaattaaatg    480
aatttttaat tataattaaa gggattaatt atatatataa gctttaatgt atttataatt    540
tttggtgtcc ncattaatat tataaaagga tgtaagtaaa aaataataat taatattaca    600
taaacaaaat aaaatgacaa tattattagg tgatattatt attaatattt taaacaaatt    660
ncngcggagt taactaaagc tgtccaatgg ncagattata atgactgcct gcnattctnc    720
aaaaggataa aacaaaagtc cacgtctagt ttgggtaaat acatgaacct ccngaatggc    780
tt    782
```

<210> SEQ ID NO 16  
<211> LENGTH: 801  
<212> TYPE: DNA  
<213> ORGANISM: Glycine max  
<220> FEATURE:  
<221> NAME/KEY: misc_feature  
<222> LOCATION: (1)..(801)  
<223> OTHER INFORMATION: n is a, c, g, or t/u

<400> SEQUENCE: 16

```
acatgattac acaagctatt taggtgacat atagaatact caagcttatg catgcggccg     60
catctagagg gcccggatcg cccttcccaa cagttgcgca gcctgaatgg cgaatggacg    120
cgccctgtag cggcgcatta agcgcggcgg gtgtggtggt tacgcgcagc gtgaccgcta    180
cacttgccag cgccctagcg cccgctcctt tcgctttctt cccttccttt ctcgccacgt    240
tcgccggctt tccccgtcaa gctctaaatc ggggctccc tttagggttc cgatttagtg    300
ctttacggca cctcgacccc aaaaaacttg attagggtga tggttcacgt antgggccat    360
```

```
cgccctgata gacngttttt cgcccttttga cnttggagtc cacgttcttt aatagtggac    420
tcttgttcca aactggaaca acactcaacc ctatctcggt ctattctttt gatttataag    480
ggattttgcc gatttcggcc tattggttaa aaaatgagct gatttaacaa aaatttnacg    540
cgaattttaa caaaatatat aacgcttacn atttcctgat ncggtatttt ctccttacnc    600
atctgtnccg tatttccacc gcatatggtg cactctcaat acaatctgct ctgatccnca    660
taatttaanc canccccgaa acccgcccaa caccccttaa aacncccttaa acgggcttgt    720 ntgctcccgg catccgctta acaaanaaac ttttaaacgt ntcccggaac ngcatntttt    780
naaagttttc acccncctcc c                                              801
```

<210> SEQ ID NO 17
<211> LENGTH: 798
<212> TYPE: DNA
<213> ORGANISM: Glycine max
<220> FEATURE:
<221> NAME/KEY: misc_feature
<222> LOCATION: (1)..(798)
<223> OTHER INFORMATION: n is a, c, g, or t/u

<400> SEQUENCE: 17

```
acatgattac gccaagctat taggtgacac tatanaatac tcaagcttat gcatgcggcc     60
gcatctagag ggcccggatc gcccttccca acagttgcgc agcctgaatg gcgaatggac    120
gcgccctgta gcggcgcatt aagcgcggcg ggtgtggtgg ttacgcncan cgtgaccgct    180
acacttgcca gcgccctagc gcccgctcct ttcgctttct tccttccctt tctcgccacg    240
ttcgccggct ttccccgtca agctctaaat cggggggctcc ctttagggtt ccgatttagt   300
gctttacggc acctcnaccc cnaaaaactt gattaggggtg atggttcacg tattgggcca   360 tcncctgat agacagtttt tcgcccnttg acgttggagt ccacgttctt taatattgga    420
ccttgttcca aactggaaca acactcaacc ctatctcggt ctattctttt gatttataag    480
ggattttgcc natttcggcc natnggttaa aaaatgagct natttaacna aaatttaacg    540
cgaattttaa caaaatattn aancttacaa tttcctnatg cgggtatttt ctccttacnc    600
atctgtgcgg tattttacaa ccgcatatgg tgcctctcaa ttacnanntg ctctgaatgc    660
cgcatatttt aaaccaacnc ngaaancccn tccaannacc cncttaacg ccccgaacgg     720 gttgntctgc cccngcatcc cttannaaac aacttttaac cttctcctgg aacttcnntt   780
tttnaaaggt ttccncn                                                   798
```

<210> SEQ ID NO 18
<211> LENGTH: 796
<212> TYPE: DNA
<213> ORGANISM: Glycine max
<220> FEATURE:
<221> NAME/KEY: misc_feature
<222> LOCATION: (1)..(796)
<223> OTHER INFORMATION: n is a, c, g, or t/u

<400> SEQUENCE: 18

```
acggnttntg aatngttatt taggtgacac tatagaaata ctcaagctta tgcatgcggc     60
cgcatctaga gggcccggat ccaccccgtc ttccactgtt cgttactacg cgagcatcnc    120
ggccctccac caccccgaca agatacttgg ccattggaat tcataaccca tcagcctgtc    180
ccacgtccct tgtgtattct ggactctaaa ctcgacctct catcatctcc gccaaacaaa    240
ctcgtcctcg tacagtggac gggccaaccc cctgaggata ctacctggga gccntggtca    300
```

-continued

| | |
|---|---|
| gaaatncctn acctttacca cctcnaggac aagtggtcct cncgggcgac ngtattgatn | 360 |
| acngttaccc ggaagatacc cagattgagc ccccacttac taagacnaag cccaacgttn | 420 |
| cccctcnaga cctgcttctt gaatgactac nanactgact cnangaagaa gctccaacca | 480 |
| ttngttnccn aagttattag ggtngttacc caattagttt agaacgttnt tccgttgaaa | 540 |
| aggctcatgt tacccccctc ncnntttttt aatncttgaa tanatnatta agaaggcctg | 600 |
| ccnnaggtta cnttactccc tccccnctct ctanatttcc tntangaagc tgccttcccc | 660 |
| cnaaattagg ggccattctc ttcctttccc gtcttttcac tccctctgc tcttatcnng | 720 |
| aattcnccctt gatnaacccc ccggtttng gatanaattg aattnacccc ccttcttgaa | 780 |
| aanagaagtt ttttcn | 796 |

<210> SEQ ID NO 19
<211> LENGTH: 808
<212> TYPE: DNA
<213> ORGANISM: Glycine max
<220> FEATURE:
<221> NAME/KEY: misc_feature
<222> LOCATION: (1)..(808)
<223> OTHER INFORMATION: n is a, c, g, or t/u

<400> SEQUENCE: 19

| | |
|---|---|
| acggcagtga ntgtaatncg actcactata gggcgaattg ccaagtcgg ccgagctcga | 60 |
| attcgtcgac ctcgagggat cgccgaagta tcgactcaac tatcagaggt agttggcgtc | 120 |
| atcgagcgcc atctcgaacc gacgttgctg gccgtacatt tgtacngctc cgcngtggat | 180 |
| ggcggcctga agccacacng tgatattgat ttgctggtta cngtgaccgt aaggcttgat | 240 |
| gaaacnacgc ggcgagcttt gatccacnat gcccatnacc nagagtagac cagaatctaa | 300 |
| cacnaatcnc attgtcngat ataacnaaat gcttttttaac acgagtgctt ccctnacan | 360 |
| tgttagattt gagcccanct cccttctcaa tgatacatnc aggatgaacn ntttgacatn | 420 |
| nctccaccna tttggnagtc tcatgcacca ccacattccc ncagtatgtt tgaaggtcnt | 480 |
| tggccngttc ccttananaa atattcctcc gccnnttcag gttgantctc attccnnaaa | 540 |
| atatatcccc ttgtccattt ccatctncaa ttcntnctgt tngaaagaac ntttgcttcc | 600 |
| agcnttcttc ccaaancnat ttttnggaaa ccctctgttt tcaagaaat tgggttcanc | 660 |
| tccaattctn tccattccna aggggttcct ccactttaac cccgnatnan caaccaaggg | 720 |
| gaattgaaaa acgggaaag ggaaaaaaat ngggcctact tncaagggaa nggcgccccc | 780 |
| tcaagnaaat ttncaaagaa gnananaa | 808 |

<210> SEQ ID NO 20
<211> LENGTH: 787
<212> TYPE: DNA
<213> ORGANISM: Glycine max
<220> FEATURE:
<221> NAME/KEY: misc_feature
<222> LOCATION: (1)..(787)
<223> OTHER INFORMATION: n is a, c, g, or t/u

<400> SEQUENCE: 20

| | |
|---|---|
| ngncgacgcc ngtgnatgac cactataggg cgaattggcc aagtcggccg agctcgaatt | 60 |
| cgtcgacctc gagggatcta tataggct tgctaagggt agagagagga agactagaga | 120 |
| tttggatcna caatgccaat aacaaagagt tnaccagaat cnaacacaaa tcncattgtc | 180 |
| ngatataaca aaatgctttt taacacgagt gcttcacata acagtgtnag atttgagccc | 240 |
| aactcctttc tcaatgatac atccnggatg gaccaatttg acatgcatca ccnatttggc | 300 |

-continued

```
agtctcatgc acaaccacat ttcccacant atgtntgang gtcattggcc ngttcactaa    360
ganaattatt cctccccagt tcangtngag tctcantccn naaatatagt ccctttgtcc    420
natttccntc tnaaatcctt cctgtggaaa gaccattgca tncagctttc tatcngaaac    480
aatatttgga aacccctctg tcttccaaga aatnggtgtc cnctcnattc tntcccatac    540
cnaagggttc atccagttta ccctgattag ancnnaaggg agtggaaana ccgggaaagg    600
aanaaaatng gccnacttcc aaggaaggcc cctccntnag aaaattttga gagagagaga    660
agagttcctt nacctttgcc tgcctcntta tattantcca gtnttatncc cncnanggtg    720
gttaccnaan ccttttccnc cnaatacngt ctnactaatt tggtactacc ccnccccttn    780 gtaccan                                                              787
```